(12) United States Patent
Botyanszki et al.

(10) Patent No.: US 12,398,131 B2
(45) Date of Patent: Aug. 26, 2025

(54) THIADIAZOLYL DERIVATIVES AS DNA POLYMERASE THETA INHIBITORS AND USES THEREOF

(71) Applicants: GlaxoSmithKline Intellectual Property (No.4) Limited, Stevenage (GB); IDEAYA Biosciences, Inc., South San Francisco, CA (US)

(72) Inventors: Janos Botyanszki, Norristown, PA (US); Kevin Duffy, Phoenixville, PA (US); Young Eun Choi, Cambridge, MA (US); Claire L. Neilan, South San Francisco, CA (US); Marcus M. Fischer, South San Francisco, CA (US)

(73) Assignees: GlaxoSmithKline Intellectual Property (No. 4) Limited, Stevenage (GB); IDEAYA Biosciences, Inc., South San Francisco, CA (US)

( * ) Notice: Subject to any disclaimer, the term of this patent is extended or adjusted under 35 U.S.C. 154(b) by 0 days.

(21) Appl. No.: 18/660,829

(22) Filed: May 10, 2024

(65) Prior Publication Data

US 2024/0327399 A1    Oct. 3, 2024

Related U.S. Application Data

(63) Continuation of application No. PCT/EP2023/084669, filed on Dec. 7, 2023.

(60) Provisional application No. 63/515,641, filed on Jul. 26, 2023, provisional application No. 63/386,709, filed on Dec. 9, 2022.

(51) Int. Cl.
| | |
|---|---|
| C07D 417/14 | (2006.01) |
| A61K 31/444 | (2006.01) |
| A61K 31/454 | (2006.01) |
| A61K 31/4545 | (2006.01) |
| A61K 31/675 | (2006.01) |
| A61P 35/00 | (2006.01) |
| C07F 9/6558 | (2006.01) |

(52) U.S. Cl.
CPC .......... *C07D 417/14* (2013.01); *A61K 31/444* (2013.01); *A61K 31/454* (2013.01); *A61K 31/4545* (2013.01); *A61K 31/675* (2013.01); *A61P 35/00* (2018.01); *C07F 9/65583* (2013.01)

(58) Field of Classification Search
CPC .. C07D 417/14; A61K 31/444; A61K 31/454; A61K 31/4545; A61K 31/675; A61P 35/00; C07F 9/65583
See application file for complete search history.

(56) References Cited

FOREIGN PATENT DOCUMENTS

| WO | 2020/243459 A1 | 12/2020 | |
|---|---|---|---|
| WO | 2022/118210 A1 | 6/2022 | |
| WO | WO-2022259204 A1 * | 12/2022 | .......... A61K 31/437 |

OTHER PUBLICATIONS

Huang, Z., Zhang, Q., Zhao, Q., Yu, W., & Chang, J. (2020). Synthesis of 2-Imino-1,3,4-thiadiazoles from Hydrazides and Isothiocyanates via Sequential Oxidation and P(NMe2)3-Mediated Annulation Reactions. Organic Letters, 22(11), 4378-4382. ( Year: 2020).*
Rodriguez et al. The Role of the Phosphorus Atom in Drug Design. Chem MedChem 2019, 14, 190. (Year: 2019).*
Anthwal T and Nain S (2022) 1,3,4-Thiadiazole Scaffold: As AntiEpileptic Agents. Front. Chem. 9:671212. (Year: 2022).*
Jain AK, Sharma S, Vaidya A, Ravichandran V, Agrawal RK. 1,3,4-thiadiazole and its derivatives: a review on recent progress in biological activities. Chem Biol Drug Des. May 2013;81(5):557-76. (Year: 2013).*
International Search Report and Written Opinion of PCT/EP2023/084669, mailed Feb. 23, 2024, International Search Authority.
U.S. Appl. No. 18/567,687, filed Dec. 6, 2023 (pending and not published), US national phase entry of PCT/IB2022/055384 (Published as WO2022/259204, Foreign Patent Documents No. 3 listed herein).
Zatreanu, D., et al. "Polθ inhibitors elicit BRCA-gene synthetic lethality and target PARP inhibitor resistance," Nature Communication 12, 3636 (2021).

* cited by examiner

*Primary Examiner* — James H Alstrum-Acevedo
*Assistant Examiner* — Pierre Paul Eleniste
(74) *Attorney, Agent, or Firm* — Alice Bradney

(57) ABSTRACT

Disclosed herein are compounds of Formula (I):

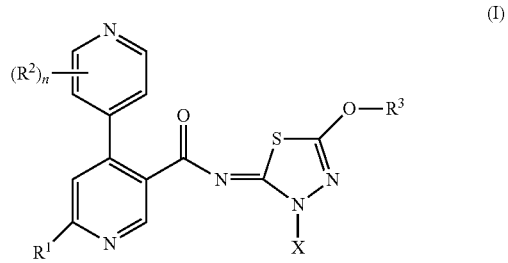

that inhibit DNA Polymerase Theta (Polθ) activity, in particular inhibit Polθ activity by inhibiting ATP dependent helicase domain activity of Polθ. Also, disclosed are pharmaceutical compositions comprising such compounds and methods of treating and/or preventing diseases treatable by inhibition of Polθ such as cancer, including homologous recombination (HR) deficient cancers.

13 Claims, 9 Drawing Sheets

THIADIAZOLYL DERIVATIVES AS DNA POLYMERASE THETA INHIBITORS AND USES THEREOF

BACKGROUND OF THE INVENTION

Targeting DNA repair deficiencies has become a proven and effective strategy in cancer treatment. However, DNA repair deficient cancers often become dependent on backup DNA repair pathways, which present an "Achilles heel" that can be targeted to eliminate cancer cells, and is the basis of synthetic lethality. Synthetic lethality is exemplified by the success of poly (ADP-ribose) polymerase (PARP) inhibitors in treating BRCA-deficient breast and ovarian cancers (Audeh M. W., et al., Lancet (2010); 376 (9737): 245-51).

DNA damage repair processes are critical for genome maintenance and stability, among which, double strand breaks (DSBs) are predominantly repaired by the nonhomologous end joining (NHEJ) pathway in G1 phase of the cell cycle and by homologous recombination (HR) in S-G2 phases. A less addressed alternative end-joining (alt-EJ), also known as microhomology-mediated end-joining (MMEJ) pathway, is commonly considered as a "backup" DSB repair pathway when NHEJ or HR are compromised. Numerous genetic studies have highlighted a role for DNA polymerase theta (Polθ, encoded by POLQ) in stimulating MMEJ in higher organisms (Chan S. H., et al., PLOS Genet. (2010); 6: e1001005; Roerink S. F., et al., Genome research. (2014); 24:954-962; Ceccaldi R., et. al., Nature (2015); 518:258-62; and Mateos-Gomez P. A., et al., Nature (2015); 518: 254-57).

Polθ is distinct among human DNA polymerases, exhibiting not only a C-terminal DNA polymerase domain but also an N-terminal helicase domain separated by a long and lesser-conserved central domain of unknown function beyond Rad51 binding (Seki eta. A1, 2003, Shima et al 2003; Yousefzadeh and Wood 2013). The N-terminal ATPase/helicase domain belongs to the HELQ class of SF2 helicase super family. In homologous recombination deficient (HRD) cells, Polθ can carry out error-prone DNA synthesis at DNA damage sites through alt-EJ pathway. It has been shown that the helicase domain of Polθ causes suppression of HR pathway through disruption of Rad51 nucleoprotein complex formation involved in initiation of the HR-dependent DNA repair reactions following ionizing radiation. This anti-recombinase activity of Polθ promotes the alt-EJ pathway. In addition, the helicase domain of Polθ contributes to microhomology-mediated strand annealing (Chan S H et al., PLOS Genet. (2010); 6: e1001005; and Kawamura K et al., Int. J. Cancer (2004); 109:9-16). Polθ efficiently promotes end-joining in alt-EJ pathway by employing this annealing activity when ssDNA overhangs contain >2 bp of microhomology (Kent T., et al., Elife (2016); 5: e13740), and Kent T., et al., Nat. Struct. Mol. Biol. (2015); 22:230-237). This reannealing activity is achieved through coupled actions of Rad51 interaction followed by ATPase-mediated displacement of Rad51 from DSB damage sites. Once annealed, the primer strand of DNA can be extended by the polymerase domain of Polθ.

The expression of Polθ is largely absent in normal cells but upregulated in breast, lung, and ovarian cancers (Ceccaldi R., et al., Nature (2015); 518, 258-62). Additionally, the increase of Polθ expression correlates with poor prognosis in breast cancer (Lemee F et al., Proc Natl Acad Sci USA. (2010); 107:13390-5). It has been shown that cancer cells with deficiency in HR, NHEJ or ATM are highly dependent on Polθ expression (Ceccaldi R., et al., Nature (2015); 518:258-62, Mateos-Gomez P A et al., Nature (2015); 518:254-57, and Wyatt D. W., et al., Mol. Cell (2016); 63:662-73). Therefore, Polθ is an attractive target for novel synthetic lethal therapy in cancers containing DNA repair defects.

SUMMARY OF THE INVENTION

Disclosed herein are certain thiadiazolyl derivatives that inhibit Polθ activity, in particular inhibit Polθ activity by inhibiting the ATP dependent helicase domain activity of Polθ. Also, disclosed are pharmaceutical compositions comprising such compounds and methods of treating and/or preventing diseases treatable by inhibition of Polθ such as cancer, including homologous recombination (HR) deficient cancers.

In one aspect, provided is a compound of Formula (I), or a pharmaceutically acceptable salt thereof:

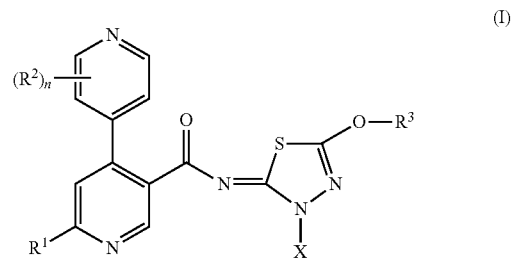

(I)

wherein X, $R^1$, $R^2$, $R^3$, and n having the meanings provided herein below.

In related aspects, provided are pharmaceutical compositions comprising a compound of Formula (I) or Table 1, or a pharmaceutically acceptable salt thereof and at least one pharmaceutically acceptable excipient.

In another aspect, provided is a method for treating and/or preventing a disease characterized by overexpression of Polθ in a patient comprising administering to the patient a therapeutically effective amount of a compound of Formula (I) or Table 1, or a pharmaceutically acceptable salt thereof (or an embodiment thereof disclosed herein). In one embodiment, the patient is in recognized need of such treatment. In another embodiment, the compound of Formula (I) or Table 1 (or an embodiment thereof disclosed herein), or a pharmaceutically acceptable salt thereof is administered in a pharmaceutical composition. In yet another embodiment, the disease is a cancer.

In still another aspect, provided is a method for treating and/or preventing a homologous recombinant (HR) deficient cancer in a patient comprising administering to the patient a therapeutically effective amount of a compound of Formula (I) or Table 1, or a pharmaceutically acceptable salt thereof (or an embodiment thereof disclosed herein). In one embodiment, the patient is in recognized need of such treatment. In another embodiment, the compound of Formula (I) or Table 1 (or an embodiment thereof disclosed herein), or a pharmaceutically acceptable salt thereof is administered in a pharmaceutical composition.

In another aspect, provided is a method for inhibiting DNA repair by Polθ in a cancer cell comprising contacting the cell with an effective amount of a compound of Formula (I) or Table 1 (or an embodiment thereof disclosed herein), or a pharmaceutically acceptable salt thereof. In one embodiment, the cancer is HR deficient cancer.

In yet another aspect, provided is a method for treating and/or preventing a cancer in a patient, wherein the cancer is characterized by a reduction or absence of BRCA1 and/or BRCA2 gene expression, the absence or mutation of BRCA1 and/or BRCA2 genes, or reduced function of BRCA1 or 2 proteins, comprising administering to the subject a therapeutically effective amount of a compound of Formula (I) or Table 1 (or an embodiment thereof disclosed herein), or a pharmaceutically acceptable salt thereof, optionally in a pharmaceutical composition.

In still another aspect, provided is a compound of Formula (I) or Table 1 (or an embodiment thereof disclosed herein), or a pharmaceutically acceptable salt thereof for inhibiting DNA repair by Polθ in a cell. In one embodiment, the cell is HR deficient cell.

In another aspect, provided is a compound of Formula (I) or Table 1 (or an embodiment thereof disclosed herein), or a pharmaceutically acceptable salt thereof for use in the treatment and/or prevention of a disease in a patient, wherein the disease is characterized by overexpression of Polθ.

In yet another aspect, provided is a compound of Formula (I) or Table 1 (or an embodiment thereof disclosed herein), or a pharmaceutically acceptable salt thereof for use in the treatment and/or prevention of a cancer in a patient, wherein the cancer is characterized by a reduction or absence of BRCA1 and/or BRCA2 gene expression, the absence or mutation of BRCA1 and/or BRCA2 genes, or reduced function of BRCA1 or 2 proteins.

In still another aspect, provided is a compound of Formula (I) or Table 1 (or an embodiment thereof disclosed herein), or a pharmaceutically acceptable salt thereof for use in the treatment and/or prevention of a HR deficient cancer in a patient.

In another aspect, provided is a compound of Formula (I) or Table 1 (or an embodiment thereof disclosed herein), or a pharmaceutically acceptable salt thereof for use in the treatment and/or prevention of a cancer that is resistant or has developed resistance to poly(ADP-ribose) polymerase (PARP) inhibitor therapy in a patient. Examples of cancers resistant to PARP-inhibitors include, but are not limited to, breast cancer, ovarian cancer, lung cancer, bladder cancer, liver cancer, head and neck cancer, pancreatic cancer, gastrointestinal cancer, and colorectal cancer.

In related aspects for the methods, uses and compositions above, the cancer is dependent on polymerase theta for proliferation, examples of which are lymphoma, rhabdoid tumor, multiple myeloma, uterine cancer, gastric cancer, peripheral nervous system cancer, rhabdomyosarcoma, bone cancer, colorectal cancer, mesothelioma, breast cancer, ovarian cancer, lung cancer, fibroblast cancer, central nervous system cancer, urinary tract cancer, upper aerodigestive cancer, leukemia, kidney cancer, skin cancer, esophageal cancer, and pancreatic cancer (https://depmap.org/portal/).

In some embodiments, a HR-deficient cancer is breast cancer. Breast cancer includes, but is not limited to, lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, mixed carcinoma, or another breast cancer, including but not limited to triple negative, HER positive, estrogen receptor positive, progesterone receptor positive, HER and estrogen receptor positive, HER and progesterone receptor positive, estrogen and progesterone receptor positive, and HER and estrogen and progesterone receptor positive. In other embodiments, HR-deficient cancer is ovarian cancer. Ovarian cancer includes, but is not limited to, epithelial ovarian carcinomas (EOC), maturing teratomas, dysgerminomas, endodermal sinus tumors, granulosa-theca tumors, Sertoli-Leydig cell tumors, and primary peritoneal carcinoma. In some embodiments, ovarian cancer includes ovarian epithelial cancer, fallopian tube cancer, and primary peritoneal cancer Also provided herein is combination therapy comprising methods of treating cancer in a subject in need thereof, the method comprising administering to the subject a therapeutically effective amount of a DNA polymerase theta (Polθ) inhibitor (e.g. a compound of Formula (I) or Formula (II)) and administering to the subject a therapeutically effective amount of a Poly ADP Ribose Polymerase (PARP) inhibitor, thereby treating the cancer in the subject.

In another aspect, provided is a method for treating and/or preventing a homologous recombinant (HR) deficient cancer in a patient in need thereof comprising contacting the cancer cells in the patient with an effective amount of a Polθ inhibitor (e.g. a compound of Formula (I) or Formula (II)) and a Poly ADP Ribose Polymerase (PARP) inhibitor. A Polθ polymerase domain inhibitor, ART4215, is developed by Artios Pharma and now in Phase 1/2a clinical trials. See "A Study of ART4215 for the Treatment of Advanced or Metastatic Solid Tumors," NCT04991480 at clinicaltrials.gov. Other Polθ polymerase domain inhibitors, including ART558, are also reported. See Zatreanu D., et al. "Polθ inhibitors elicit BRCA-gene synthetic lethality and target PARP inhibitor resistance," NATURE COMMUNICATIONS, 2021. 12(1): 3636.

A compound of Formula (II) has the structure

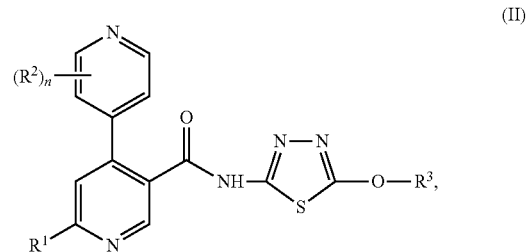

or a pharmaceutically acceptable salt thereof,
wherein $R^1$, $R^2$, $R^3$, and n having the meanings provided herein below.

In some aspects, provided herein are methods of treating cancer in a subject in need thereof, the methods comprising administering to the subject a combination comprising a DNA polymerase theta (Polθ) inhibitor (e.g. a compound of Formula (I) or Formula (II)) and a Poly ADP Ribose Polymerase (PARP) inhibitor, together with at least a pharmaceutically acceptable carrier, thereby treating the cancer in the subject.

A compound of Formula (I), or a pharmaceutically acceptable salt thereof, for use in therapy.

A combination of a compound of Formula (I) or Formula (II) and a Poly ADP Ribose Polymerase (PARP) inhibitor, for use in therapy.

DETAILED DESCRIPTION

Figure 1:
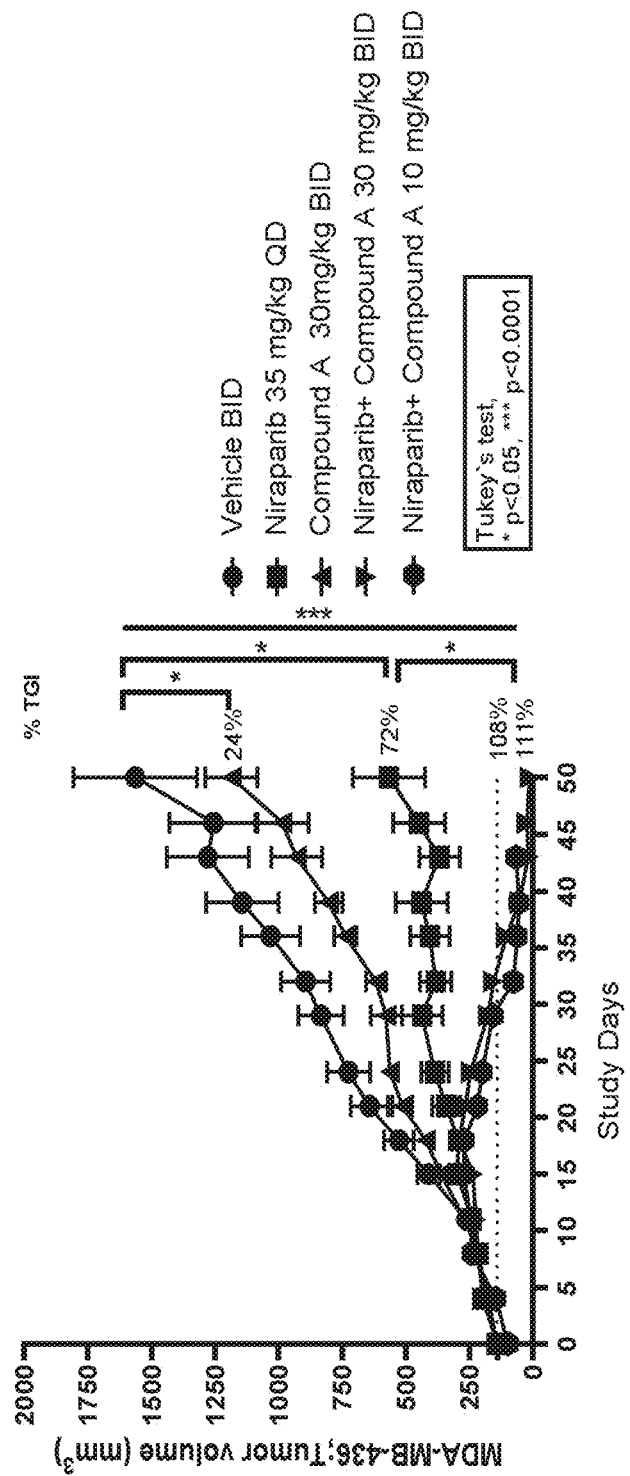
FIG. 1 displays an efficacy study of Compound A in BRCA1 mutant TNBC MDA-MB-436 model. The dotted line represents the mean starting tumor volume. Mixed effects model with Tukey test was applied to calculate statistics, *p<0.05 after adjustment for multiplicity.

Before the present invention is further described, it is to be understood that the invention is not limited to the particular embodiments set forth herein, and it is also to be understood that the terminology used herein is for the purpose of describing particular embodiments only, and is not intended to be limiting.

The singular forms "a," "an," and "the" as used herein and in the appended claims include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

When needed, any definition herein may be used in combination with any other definition to describe a composite structural group. By convention, the trailing element of any such definition is that which attaches to the parent moiety. For example, the composite group alkoxyalkyl means that an alkoxy group is attached to the parent molecule through an alkyl group.

The publications discussed herein are provided solely for their disclosure prior to the filing date of the present application. Further, the dates of publication provided may be different from the actual publication dates, which may need to be independently confirmed.

Definitions

Unless otherwise stated, the following terms used in the specification and claims are defined for the purposes of this Application and have the following meaning:

The term "alkyl", by itself or as part of another substituent, means, unless otherwise stated, a saturated straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene, hexylene, and the like.

The term "alkoxy" refers to an alkyl group having an oxygen atom that connects the alkyl group to the point of attachment: alkyl-O—. As for an alkyl group, alkoxy groups can have any suitable number of carbon atoms, such as $C_{1-6}$, and can be straight or branched. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

The term "heterocycloalkyl" refers to a saturated or partially unsaturated monocyclic ring having the indicated number of ring vertices (e.g., a 3- to 7-membered ring) and having from one to five heteroatoms selected from N, O, and S as ring vertices. For example, "heterocycloalkyl" refers to a saturated or partially unsaturated monocyclic ring having 4 to 6 ring members and from 1 to 3 heteroatoms as ring vertices independently selected from N, O, and S. Partially unsaturated heterocycloalkyl groups have one or more double or triple bonds in the ring, but heterocycloalkyl group are not aromatic. Heterocycloalkyl groups can include any number of ring atoms, such as, 3 to 6, 4 to 6, 5 to 6, 3 to 7, 4 to 7, or 5 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Non-limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. Further non-limiting examples of heterocycloalkyl groups include pyrrolidine, imidazolidine, pyrazolidine, butyrolactam, valerolactam, imidazolidinone, hydantoin, dioxolane, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, and the like. A heterocycloalkyl group can be attached to the remainder of the molecule through a ring carbon or a heteroatom.

The terms "halo" or "halogen," by themselves or as part of another substituent, mean, unless otherwise stated, a fluorine, chlorine, bromine, or iodine atom.

The term "haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, the term "$C_{1-4}$ haloalkyl" is meant to include trifluoromethyl, 2,2,2-trifluoroethyl, 4-chlorobutyl, 3-bromopropyl, and the like.

The term "haloalkoxy" refers to an alkoxy group where some or all of the hydrogen atoms are substituted with halogen atoms. As for an alkyl group, haloalkoxy groups can have any suitable number of carbon atoms, such as $C_{1-6}$, and can be straight or branched, and are substituted with 1, 2, 3, or more halogens. When all the hydrogens are replaced with a halogen, for example by fluorine, the compounds are per-substituted, for example, perfluorinated Haloalkoxy includes, but is not limited to, trifluoromethoxy, 2,2,2,-trifluoroethoxy, perfluoroethoxy, etc.

As used herein, the term "heteroatom" is meant to include oxygen (O), nitrogen (N), and sulfur (S).

The term "pharmaceutically acceptable salt" is meant to include a salt of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs are those compounds that readily undergo chemical changes under physiological conditions to provide the parent compounds. Additionally, prodrugs can be converted to the parent compounds by chemical or biochemical methods in an ex vivo environment. The term "prodrug moiety" refers to the chemical moiety of a prodrug that is cleaved under physiological conditions to form the active parent compound.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are intended to be within the scope of the present invention.

Certain compounds of the present invention possess asymmetric carbon atoms (optical centers) or double bonds; the racemates, diastereomers, geometric isomers, and individual isomers (e.g., separate enantiomers) are all intended to be encompassed within the scope of the present invention. When a stereochemical depiction is shown, it is meant to refer the compound in which one of the isomers is present and substantially free of the other isomer. "Substantially free of" another isomer indicates at least an 80/20 ratio of the two isomers, more preferably 90/10, or 95/5 or more. In some embodiments, one of the isomers will be present in an amount of at least 99%.

The present invention also includes all suitable isotopic variations of a compound of formula (I) of Table 1, or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^{2}H$, $^{3}H$, $^{13}C$, $^{14}C$, $^{15}N$, $^{17}O$, $^{18}O$, $^{18}F$ and $^{36}Cl$, respectively. Certain isotopic variations of a compound of formula (I) or a salt or solvate thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Thus, in one embodiment, the present invention includes the compounds of Table 1 (e.g. Example 1) wherein one or more hydrogen atoms attached to carbon atoms are replaced by deuterium. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

The terms "patient" or "subject" are used interchangeably to refer to a human or a non-human animal (e.g., a mammal). In one embodiment, the patient is human.

The terms "administration," "administer" and the like, as they apply to, for example, a subject, cell, tissue, organ, or biological fluid, refer to contact of, for example, an Polθ inhibitor, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat," "treating." "treatment" and the like refer to a course of action (such as administering a Polθ inhibitor or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" or "in need thereof" as used herein refers to a judgment made by a physician or other caregiver that a subject requires or will benefit from treatment. This judgment is made based on a variety of factors that are in the realm of the physician's or caregiver's expertise. For example, the patient has been diagnosed as having a disease linked to overexpression of Polθ or a homologous recombination (HR)-deficient cancer.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an Polθ inhibitor (or, e.g., a metabolite thereof) at a particular time post-administration may be indicative of whether a therapeutically effective amount has been used.

The terms "inhibitors" and "activators" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like.

"Pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable excipient" as used in the specification and claims includes both one and more than one such excipient.

As used herein, a wavy line, "⁓", that intersects a single, double or triple bond in any chemical structure depicted herein, represents the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible.

"About", as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

"Disease" as used herein is intended to be generally synonymous, and is used interchangeably with, the terms "disorder", "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

"Patient" is generally synonymous with the term "subject" and as used herein includes all mammals including humans. Preferably, the patient is a human.

"Inhibiting", "reducing," or any variation of these terms in relation of Polθ, includes any measurable decrease or complete inhibition to achieve a desired result. For example, there may be a decrease of about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of Polθ activity compared to its normal activity.

The term "homologous recombination" refers to the cellular process of genetic recombination in which nucleotide sequences are exchanged between two similar or identical DNA.

The term "homologous recombination (HR) deficient cancer" refers to a cancer that is characterized by a reduction or absence of a functional HR repair pathway. HR deficiency may arise from absence of one or more HR-associated genes or presence of one or more mutations in one or more HR-associated genes. Examples of HR-associated genes include BRCA1, BRCA2, RAD54, RAD51B, Ct1P (Choline Transporter-Like Protein), PALB2 (Partner and Localizer of BRCA2), XRCC2 (X-ray repair complementing defective repair in Chinese hamster cells 2), RECQL4 (RecQ Protein-Like 4), BLM (Bloom syndrome, RecQ helicase-like), WRN (Werner syndrome, one or more HR-associated genes) Nbs 1 (Nibrin), and genes encoding Fanconi anemia (FA) proteins or FA-like genes e.g, FANCA, FANCB, FANCC, FANCD1 (BRCA2), FANCD2, FANCE, FANCF, FANCG, FANCI, FANJ (BRIP1), FANCL, FANCM, FANCN (RALB2), FANCP (SLX4), FANCS (BRCA1), RAD51C, and XPF.

The term "Polθ overexpression" refers to the increased expression or activity of Polθ in a diseased cell e.g., cancerous cell, relative to expression or activity of Polθ in a normal cell (e.g., non-diseased cell of the same kind). The amount of Polθ can be at least 2-fold, at least 3-fold, at least 4-fold, at least 5-fold, at least 10-fold, or more relative to the Polθ expression in a normal cell. Examples of Polθ cancers include, but are not limited to, breast, ovarian, cervical, lung, colorectal, gastric, bladder and prostate cancers.

As used herein, "Poly ADP Ribose Polymerase (PARP) inhibitor" refers to an agent that inhibits PARP activity, including PARP1 and PARP2. Examples of PARP inhibitors include, but are not limited to, niraparib, rucaparib, olaparib, talazoparib, and veliparib.

Compounds:

In some aspects, provided herein is a compound of Formula (I):

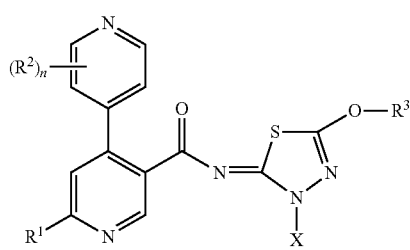

(I)

wherein:

$R^1$ is H, halo, $C_{1-4}$ alkyl, $C_{1-4}$ alkoxy, $C_{1-4}$ haloalkyl, or $C_{1-4}$ haloalkoxy;

each $R^2$ is independently halo, $C_{1-4}$ alkyl, $C_{1-4}$ haloalkyl, $C_{1-4}$ alkoxy, or $C_{1-4}$ haloalkoxy;

X is a prodrug moiety;

$R^3$ is $C_{1-4}$ alkyl, $C_{1-4}$ haloalkyl, $C_{3-6}$ cycloalkyl, or heterocycloalkyl, wherein said $C_{3-6}$ cycloalkyl and said heterocycloalkyl are optionally substituted with 1 to 4 $R^{3a}$ substituents, each of which is independently selected from halo, $C_{1-4}$ alkyl, $C_{1-4}$ haloalkyl, $C_{1-4}$ haloalkoxy, -$L^3$-O-$C_{1-4}$ alkyl, -$L^3$-OH, and oxo;

each $L^3$ is independently selected from a bond and $C_{1-4}$ alkylene;

each heterocycloalkyl has from 4 to 6 ring members and from 1 to 3 heteroatoms as ring vertices independently selected from N, O, and S; and n is 0, 1, 2, or 3;

or a pharmaceutically acceptable salt thereof.

In some embodiments, X in Formula (I) or a subembodiment thereof is —CH($R^c$)—O—P(O)(O$R^a$)(O$R^b$), —CH($R^c$)—O—C(O)—$C_{1-6}$ alkylene-CO$_2$H, —CH($R^c$)—O—C(O)—$C_{1-6}$ alkylene-O—P(O)(O$R^a$)(O$R^b$), —CH($R^c$)—O—C(O)—$C_{1-6}$ alkylene-P(O)(O$R^a$)(O$R^b$), —CH($R^c$)—O—C(O)—$C_{1-6}$ alkylene-NR$^a$R$^b$, or —CH($R^c$)—O—C(O)—$C_{1-6}$ alkylene-heterocycloalkyl, wherein $R^a$ and $R^b$ are each independently H or $C_{1-4}$ alkyl, and $R^c$ is independently selected from hydrogen and methyl.

In some embodiments, X in Formula (I) or a subembodiment thereof is —CH$_2$O—P(O)(O$R^a$)(O$R^b$), —CH$_2$—O—C(O)—$C_{1-6}$ alkylene-CO$_2$H,
—CH$_2$—O—C(O)—$C_{1-6}$ alkylene-O—P(O)(O$R^a$)(O$R^b$),
—CH$_2$—O—C(O)—$C_{1-6}$ alkylene-P(O)(O$R^a$)(O$R^b$),
—CH$_2$—O—C(O)—$C_{1-6}$ alkylene-NR$^a$R$^b$,
or —CH$_2$—O—C(O)—$C_{1-6}$ alkylene-heterocycloalkyl, wherein $R^a$ and $R^b$ are each independently H or $C_{1-4}$ alkyl.

In some embodiments, X in Formula (I) or a subembodiment thereof is —CH$_2$O—P(O)(O$R^a$)(O$R^b$), —CH$_2$—O—C(O)—$C_{1-6}$ alkylene-CO$_2$H, or —CH$_2$—O—C(O)—$C_{1-6}$ alkylene-P(O) (O$R^a$)(O$R^b$).

In some embodiments, X in Formula (I) or a subembodiment thereof is —CH$_2$O—P(O)(O$R^a$)(O$R^b$) or —CH$_2$—O—C(O)—$C_{1-6}$ alkylene-CO$_2$H.

In some embodiments, X in Formula (I) or a subembodiment thereof is —CH$_2$—O—C(O)—$C_{1-6}$ alkylene-piperidinyl.

In some embodiments, X in Formula (I) or a subembodiment thereof is —CH$_2$O—P(O) (O$R^a$)(O$R^b$).

In some embodiments, X in Formula (I) or a subembodiment thereof is —CH$_2$—O—C(O)—$C_{1-6}$ alkylene CO$_2$H.

In some embodiments, X in Formula (I) or a subembodiment thereof is

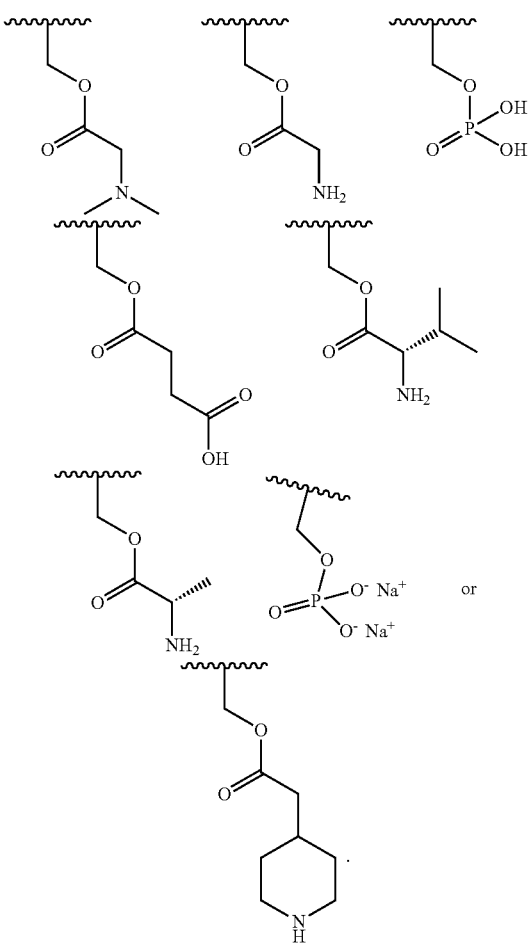

In some embodiments, X in Formula (I) or a subembodiment thereof is

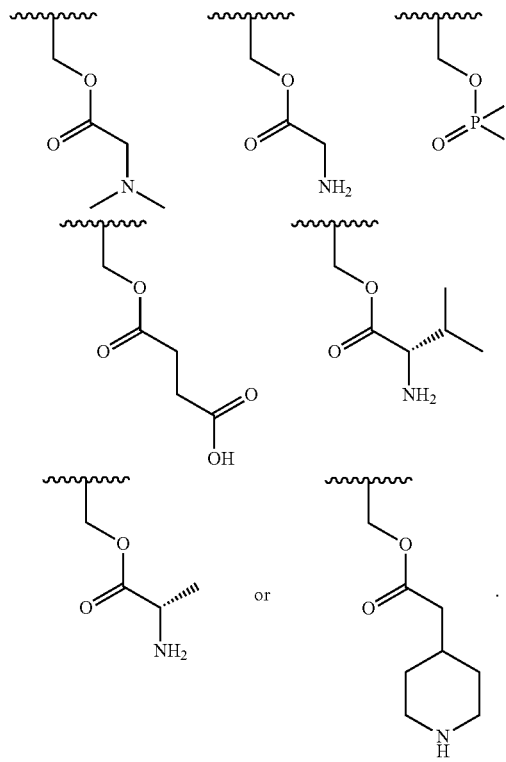

In some embodiments, X in Formula (I) or a subembodiment thereof is

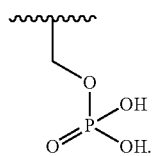 [SMILES: *COP(=O)(O)O]

In some embodiments, X in Formula (I) or a subembodiment thereof is

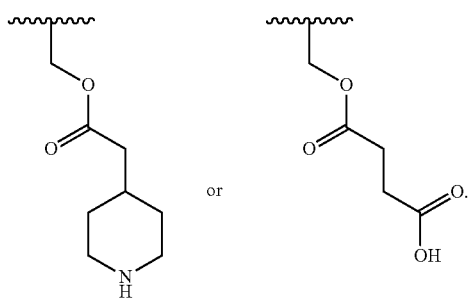 [SMILES: *COC(=O)CC1CCNCC1 ; "or" ; *COC(=O)CCC(=O)O]

In some embodiments, X in Formula (I) or a subembodiment thereof is

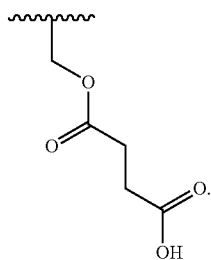 [SMILES: *COC(=O)CCC(=O)O]

In some embodiments, X in Formula (I) or a subembodiment thereof is

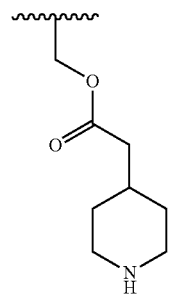

In some embodiments, $R^1$ in Formula (I) or a subembodiment thereof is $C_{1-4}$ alkyl. In some embodiments, $R^1$ in Formula (I) or a subembodiment thereof is methyl.

In some embodiments, each $R^2$ in Formula (I) or a subembodiment thereof is independently halo, $C_{1-4}$ alkoxy, or $C_{1-4}$ haloalkoxy. In some embodiments, each $R^2$ in Formula (I) or a subembodiment thereof is independently halo or $C_{1-4}$ alkoxy. In some embodiments, each $R^2$ in Formula (I) or a subembodiment thereof is independently F, Cl, or methoxy. In some embodiments, n in Formula (I) or a subembodiment thereof is 2 and two $R^2$ are Cl and methoxy.

In some embodiments, n in Formula (I) or a subembodiment thereof is 1, 2, or 3. In some embodiments, n in Formula (I) or a subembodiment thereof is 1. In some embodiments, n in Formula (I) or a subembodiment thereof is 2. In some embodiments, n in Formula (I) or a subembodiment thereof is 3.

In some embodiments, n in Formula (I) or a subembodiment thereof is 2, and two $R^2$ are halo and methoxy.

In some embodiments, $R^3$ in Formula (I) or a subembodiment thereof is $C_{1-4}$ alkyl or $C_{1-4}$ haloalkyl. In some embodiments, $R^3$ in Formula (I) or a subembodiment thereof is $C_{1-4}$ alkyl. In some embodiments, $R^3$ in Formula (I) or a subembodiment thereof is methyl.

In some embodiments, $R^3$ in Formula (I) or a subembodiment thereof is $C_{3-6}$ cycloalkyl or heterocycloalkyl, wherein said $C_{3-6}$ cycloalkyl and said heterocycloalkyl are optionally substituted with 1 to 4 $R^{3a}$ substituents, each of which is independently selected from halo, $C_{1-4}$ alkyl, $C_{1-4}$ haloalkyl, $C_{1-4}$ haloalkoxy, -$L^3$-O-$C_{1-4}$ alkyl, -$L^3$-OH, and oxo.

In some embodiments, the compound of Formula (I) has the structure:

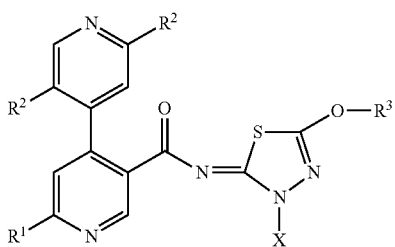

(I-a)

wherein X, R[1], R[2], and R[3] have the meanings provided herein. In some embodiments, R[1] is $C_{1-4}$ alkyl, each R[2] is independently halo, $C_{1-4}$ alkoxy, or $C_{1-4}$ haloalkoxy, and R[3] is $C_{1-4}$ alkyl.

In some embodiments, the compound of Formula (I) has the structure:

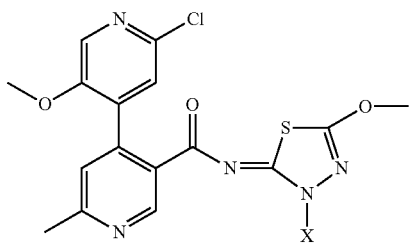

(I-b)

wherein X has the meaning provided herein.

The compounds of the present disclosure may exist in tautomeric forms. It is to be understood that any reference to a named compound or a structurally depicted compound is intended to encompass all tautomers of such compound.

Representative compounds of Formula (I) are listed in Table 1 below.

TABLE 1

| Cpd # | Structure |
|---|---|
| 1 | 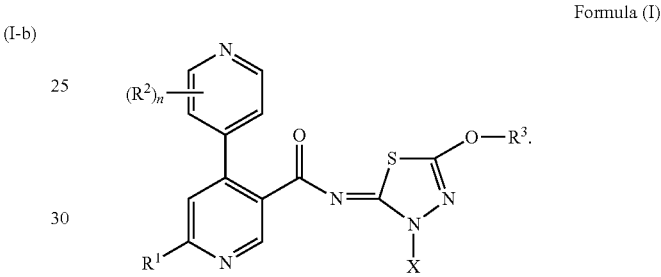 |
| 2 | 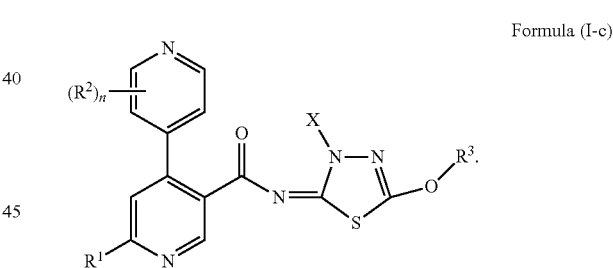 |

TABLE 1-continued

| Cpd # | Structure |
|---|---|
| 3 | 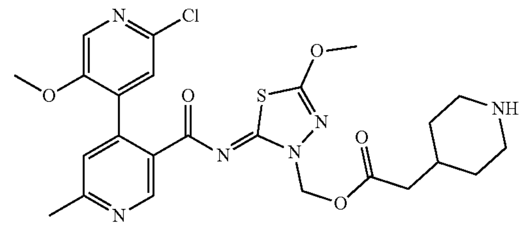 [SMILES: COc1nn(COC(=O)CC2CCNCC2)/c(=N/C(=O)c2cnc(C)cc2-c2cc(Cl)ncc2OC)s1] |

In some embodiments, the compound of the present invention is a compound from Table 1.

The compounds of Formula (I) are depicted as a (Z) isomer with respect to the double bond between the thiadiazole moiety and the nitrogen in the amide group:

Formula (I)

The compound of Formula (I) is also intended to encompass the compounds of Formula (I-c), an (E) isomer:

Formula (I-c)

Pharmaceutical Composition

The compounds of Formula (I) or Table 1, or a pharmaceutically acceptable salt thereof, provided herein may be in the form of compositions suitable for administration to a subject. In general, such compositions are pharmaceutical compositions comprising a compound of Formula (I) or Table 1, or a pharmaceutically acceptable salt thereof and one or more pharmaceutically acceptable excipients. The pharmaceutical compositions may be used in all the methods disclosed herein; thus, for example, the pharmaceutical compositions can be administered ex vivo or in vivo to a subject in order to practice the therapeutic methods and uses described herein.

The pharmaceutical compositions can be formulated to be compatible with the intended method or route of administration; exemplary routes of administration are set forth herein. Furthermore, the pharmaceutical compositions may be used in combination with other therapeutically active agents or compounds as described herein in order to treat the diseases, disorders and conditions contemplated by the present disclosure.

The pharmaceutical compositions containing the active ingredient (e.g., a compound of Formula (I) or Table 1, a pharmaceutically acceptable salt thereof) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets, capsules, and the like. These excipients may be, for example, diluents, such as calcium carbonate, sodium carbonate, lactose, calcium phosphate or sodium phosphate; granulating and disintegrating agents, for example, corn starch, or alginic acid, binding agents, for example starch, gelatin or acacia, and lubricating agents, for example magnesium stearate, stearic acid or talc.

The pharmaceutical compositions typically comprise a therapeutically effective amount of a compound of Formula (I) or Table 1, or a pharmaceutically acceptable salt thereof, and one or more pharmaceutically acceptable excipient. Suitable pharmaceutically acceptable excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino) propanesulfonic acid (MOPS), and N-tris[Hydroxymethyl]methyl-3-aminopropanesulfonic acid (TAPS).

All the compounds and pharmaceutical compositions provided herein can be used in all the methods provided herein. For example, the compounds and pharmaceutical compositions provided herein can be used in all the methods for treatment and/or prevention of all diseases or disorders provided herein. Thus, the compounds and pharmaceutical compositions provided herein are for use as a medicament.

Routes of Administration

Compounds of Formula (I) or Table 1, or a pharmaceutically acceptable salt thereof and compositions containing the same may be administered in any appropriate manner. Suitable routes of administration include oral, parenteral (e.g., intramuscular, intravenous, subcutaneous (e.g., injection or implant), intraperitoneal, intracisternal, intraarticular, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to administer the compounds of Formula (I) or Table 1, or a pharmaceutically acceptable salt thereof over a defined period of time. Particular embodiments of the present invention contemplate oral administration.

Dosing

The compounds of Formula (I) or Table 1, or a pharmaceutically acceptable salt thereof provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

Combinations of Polθ Inhibitors and Poly ADP Ribose Polymerase (PARP) Inhibitors The combination of agents described in this section may display a synergistic effect. The term "synergistic effect" or "synergy" as used herein, refers to action of two agents, for example, a DNA polymerase theta (Polθ) inhibitor (e.g. a compound of Formula (I) or Formula (II)) and a Poly ADP Ribose Polymerase (PARP) inhibitor producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6:429-453 (1981)), the equation of Loewe additivity (Loewe, S. and Muischnek, H., Arch. Exp. Pathol Pharmacol. 114; 313-326 (1926)) and the median-effect equation (Chou, T. C. and Talalay, P., Adv. Enzyme Regul. 22:27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In some aspects, provided herein is a combination therapy comprising a therapeutically effective amount of a Polθ inhibitor (e.g. a compound of Formula (I) or Formula (II)) and a PARP inhibitor. A "therapeutically effective amount" of a combination of agents (i.e., a Polo inhibitor of Formula (I) or Formula (II) and a PARP inhibitor) is an amount sufficient to provide an observable improvement over the baseline clinically observable signs and symptoms of the disorders treated with the combination. Observable improvements include those that can be visually ascertained by a clinician and biological tests, biopsies, and assays.

In some aspects, provided herein are methods of treating cancer in a subject in need thereof, the method comprising administering to the subject a therapeutically effective amount of a Polθ inhibitor of Formula (I) or Formula (II) and administering to the subject a therapeutically effective amount of a PARP inhibitor, thereby treating the cancer in the subject.

In another aspect, provided is a method for treating and/or preventing a homologous recombinant (HR) deficient cancer in a patient comprising administering to the patient an effective amount of a compound of Formula (I) and administering to the patient an effective amount of a Poly ADP Ribose Polymerase (PARP) inhibitor. In one embodiment, the method for treating and/or preventing a homologous recombinant (HR) deficient cancer in a patient in need thereof comprises administering to the patient an effective amount of the compound Example 1 and administering to the patient an effective amount of niraparib.

In one embodiment, the method for treating and/or preventing a homologous recombinant (HR) deficient cancer in a patient in need thereof comprises administering to the patient an effective amount of the compound Example 1 and administering to the patient an effective amount of olaparib.

In another aspect, provided is a method for treating and/or preventing a homologous recombinant (HR) deficient cancer in a patient comprising contacting the cancer cells in the patient with an effective amount of a compound of Formula (II) and an effective amount of a Poly ADP Ribose Polymerase (PARP) inhibitor. In one embodiment, the method for treating and/or preventing a homologous recombinant (HR) deficient cancer in a patient in need thereof comprises contacting the cancel cells in the patient with an effective amount of Compound A and an effective amount of niraparib.

In one embodiment, the method for treating and/or preventing a homologous recombinant (HR) deficient cancer in a patient in need thereof comprises contacting the cancel cells in the patient with an effective amount of Compound A and an effective amount of olaparib.

In some aspects, provided herein are methods of treating cancer in a subject in need thereof, the methods comprising administering to the subject a combination comprising a Polθ inhibitor of Formula (I) or Formula (II) and a PARP inhibitor, together with at least a pharmaceutically acceptable carrier, thereby treating the cancer in the subject.

In some aspects, use of a combination of a Polθ inhibitor of Formula (I) or Formula (II) and a PARP inhibitor for the manufacture of a medicament is provided.

In another embodiment, use of a combination of a Polθ inhibitor of Formula (I) or (II) and a PARP inhibitor for the treatment of cancer is provided.

In some embodiments, the cancer is characterized as a homologous recombinant (HR) deficient cancer.

In some embodiments, the Polθ inhibitor is an inhibitor of the ATPase domain of Polθ.

In some embodiments, the cancer is characterized by a reduction or absence of BRCA1 and/or BRCA2 gene expression, the absence of BRCA1 and/or BRCA2 genes, absence or mutation of BRCA1 and/or BRCA2 proteins, reduced function of BRCA1 and/or BRCA2 protein, or a combination thereof.

Polθ Inhibitors for Combination Therapy with a PARP Inhibitor

In some embodiments, Polθ inhibitors suitable for the combination therapy treatment with PARP inhibitors described in this section are compounds of Formula (II)

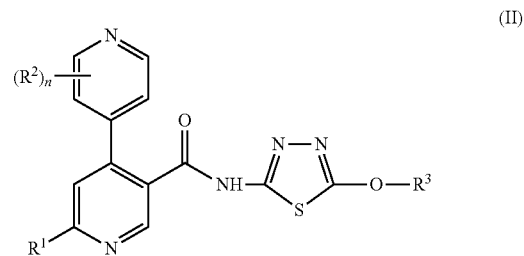

(II)

wherein:
$R^1$ is H, halo, $C_{1-4}$ alkyl, $C_{1-4}$ alkoxy, $C_{1-4}$ haloalkyl, or $C_{1-4}$ haloalkoxy;
each $R^2$ is independently halo, $C_{1-4}$ alkyl, $C_{1-4}$ haloalkyl, $C_{1-4}$ alkoxy, or $C_{1-4}$ haloalkoxy;
$R^3$ is $C_{1-4}$ alkyl, $C_{1-4}$ haloalkyl, $C_{3-6}$ cycloalkyl, or heterocycloalkyl, wherein said $C_{3-6}$ cycloalkyl and said heterocycloalkyl are optionally substituted with 1 to 4 $R^{3a}$ substituents, each of which is independently selected from halo, $C_{1-4}$ alkyl, $C_{1-4}$ haloalkyl, $C_{1-4}$ haloalkoxy, -$L^3$-O—$C_{1-4}$ alkyl, -$L^3$-OH, and oxo;
each $L^3$ is independently selected from a bond and $C_{1-4}$ alkylene;
each heterocycloalkyl has from 4 to 6 ring members and from 1 to 3 heteroatoms as ring vertices independently selected from N, O, and S; and
n is 0, 1, 2, or 3;
or a pharmaceutically acceptable salt thereof.

In some embodiments, $R^1$ in Formula (II) or subembodiments thereof is $C_{1-4}$ alkyl. In some embodiments, $R^1$ in Formula (II) or subembodiments thereof is methyl.

In some embodiments, each $R^2$ in Formula (II) or subembodiments thereof is halo, $C_{1-4}$ alkoxy, or $C_{1-4}$ haloalkoxy. In some embodiments, each $R^2$ in Formula (II) or subembodiments thereof is independently halo or $C_{1-4}$ alkoxy. In some embodiments, each $R^2$ in Formula (I) or a subembodiment thereof is independently F, Cl, or methoxy. In some embodiments, n in Formula (I) or a subembodiment thereof is 2 and two $R^2$ are Cl and methoxy.

In some embodiments, n in Formula (II) or a subembodiment thereof is 1, 2, or 3. In some embodiments, n in Formula (II) or a subembodiment thereof is 1. In some embodiments, n in Formula (II) or a subembodiment thereof is 2. In some embodiments, n in Formula (II) or a subembodiment thereof is 3.

In some embodiments, n in Formula (II) or a subembodiment thereof is 2, and two $R^2$ are halo and methoxy.

In some embodiments, $R^3$ in Formula (II) or a subembodiment thereof is $C_{1-4}$ alkyl or $C_{1-4}$ haloalkyl. In some embodiments, $R^3$ in Formula (II) or a subembodiment thereof is $C_{1-4}$ alkyl. In some embodiments, $R^3$ in Formula (II) or a subembodiment thereof is methyl.

In some embodiments, $R^3$ in Formula (II) or a subembodiment thereof is $C_{3-6}$ cycloalkyl or heterocycloalkyl, wherein said $C_{3-6}$ cycloalkyl and said heterocycloalkyl are optionally substituted with 1 to 4 $R^{3a}$ substituents, each of which is independently selected from halo, $C_{1-4}$ alkyl, $C_{1-4}$ haloalkyl, $C_{1-4}$ haloalkoxy, -$L^3$-O—$C_{1-4}$ alkyl, -$L^3$-OH, and oxo.

In some embodiments, the Polθ inhibitor of Formula (II) is

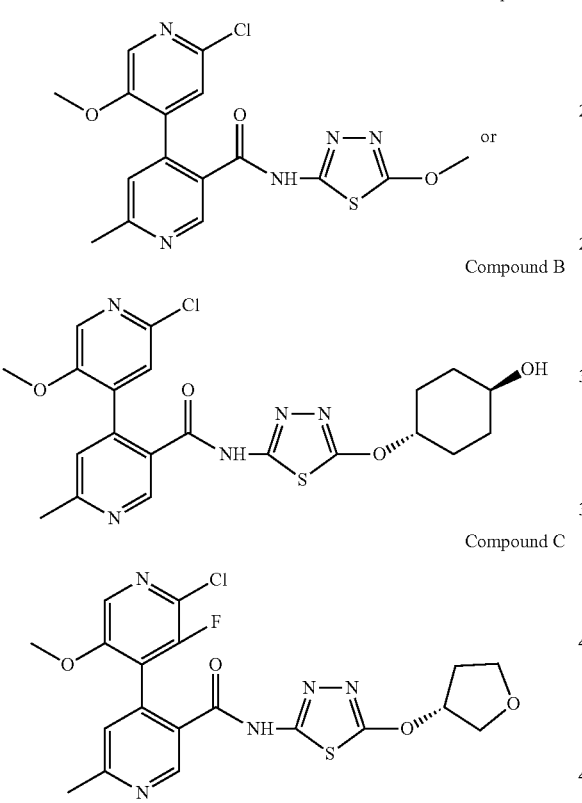

Compound A

Compound B

Compound C

In some embodiments, the Polθ inhibitor of Formula (II) is Compound A:

Compound A

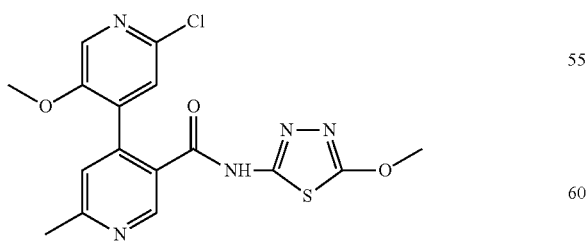

or a pharmaceutically acceptable salt thereof.

In some embodiments, Polθ inhibitors suitable for the combination therapy treatment with PARP inhibitors described in this section are compounds of Formula (I), or a pharmaceutically acceptable salt thereof. In some embodiments, the Polθ inhibitor of Formula (I) is the compound of Example 1 ("Example 1"):

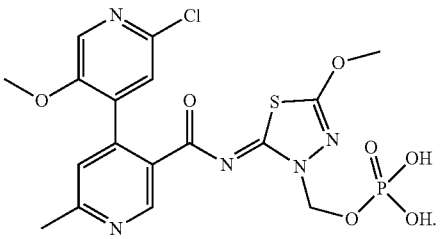 [SMILES: COc1nn(COP(=O)(O)O)/c(=N/C(=O)c2cnc(C)cc2-c2cc(Cl)ncc2OC)s1]

In some embodiments, the Polθ inhibitor for combination therapy is ART558 having the structure:

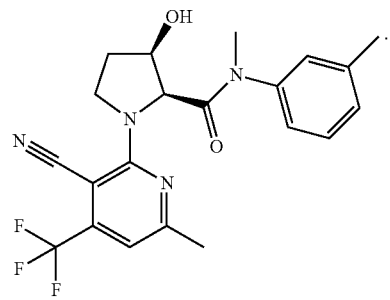 [SMILES: Cc1cccc(N(C)C(=O)[C@@H]2[C@H](O)CCN2c2nc(C)cc(C(F)(F)F)c2C#N)c1]

In some embodiments, the Polθ inhibitor for combination therapy is ART4215.

PARP Inhibitors for Combination Therapy with Polθ Inhibitors

The combination therapy described herein provides PARP inhibitors for use with a Polθ inhibitor (e.g. a compound of Formula (I) or Formula (II)). A number of agents with PARP inhibitory activity and methods of making the same are known in the art. Each of these embraced by this disclosure. In some embodiments, the PARP inhibitor is

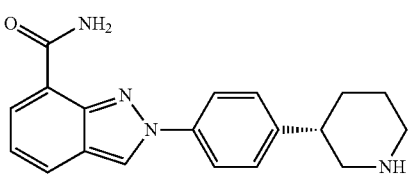

Niraparib

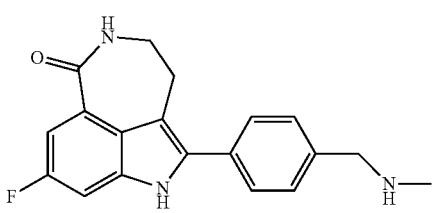

Rucaparib

-continued

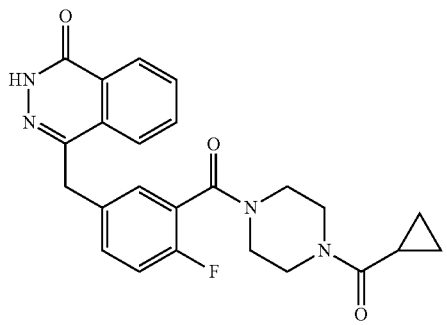
Olaparib

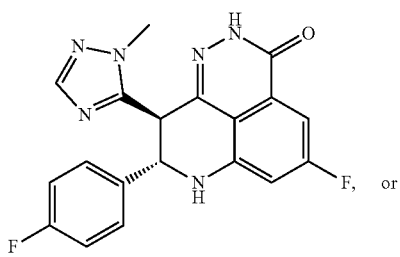
Talazoparib

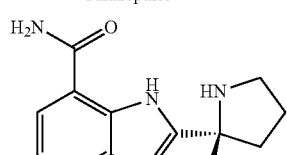
Veliparib or a pharmaceutically acceptable salt thereof, or a hydrate thereof.

In some embodiments, the PARP inhibitor is

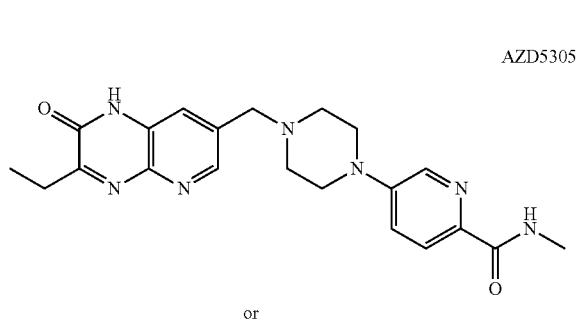
AZD5305 or

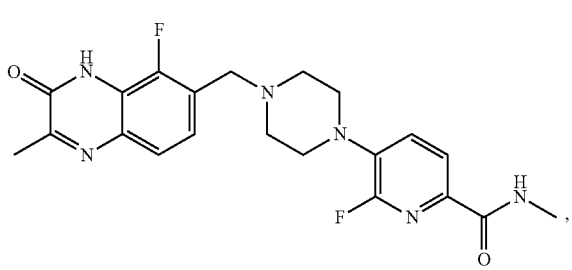
AZD9574 or pharmaceutically acceptable salt thereof, or a hydrate thereof.

Select Combination Therapy Embodiments

Embodiment 1. A method of treating cancer in a subject in need thereof, the method comprising administering to the subject a therapeutically effective amount of a Polθ inhibitor, or a pharmaceutically acceptable salt thereof, and administering to the subject a therapeutically effective amount of a PARP inhibitor, or a pharmaceutically acceptable salt thereof.

Embodiment 1a. The method of embodiment 1, wherein the Polθ inhibitor is an inhibitor of ATPase domain of Polθ.

Embodiment 2. The method of embodiment 1, wherein the Polθ inhibitor is a compound of Formula (I) as defined herein, or a pharmaceutically acceptable salt thereof.

Embodiment 3. The method of embodiment 2, wherein the Polθ inhibitor is the compound of Example 1, having the structure:

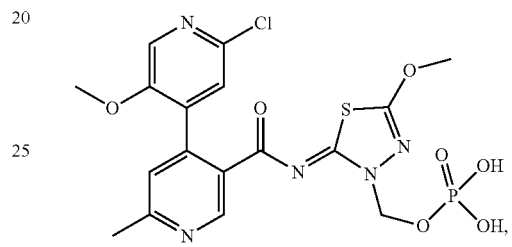

or a pharmaceutically acceptable salt thereof.

Embodiment 4. The method of embodiment 1, wherein the Polθ inhibitor is a compound of Formula (II) as defined herein, or a pharmaceutically acceptable salt thereof.

Embodiment 5. The method of embodiment 2, wherein the Polθ inhibitor is Compound A

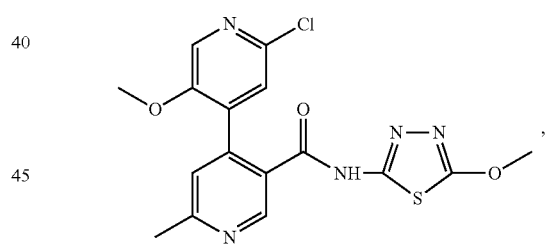

or a pharmaceutically acceptable salt thereof.

Embodiment 6. The method of embodiment 1, wherein the Polθ inhibitor is ART558 or ART4215, or a pharmaceutically acceptable salt thereof.

Embodiment 7. The method of any one of embodiments 1-6, wherein the PARP inhibitor is selected from the group consisting of Niraparib, Rucaparib, Olaparib, Talazoparib, and Veliparib, or a pharmaceutically acceptable salt thereof, or a hydrate thereof.

Embodiment 8. The method of any one of embodiments 1-6, wherein the PARP inhibitor is niraparib, preferably niraparib tosylate monohydrate.

Embodiment 9 The method of any one of embodiments 1-6, wherein the PARP inhibitor is:

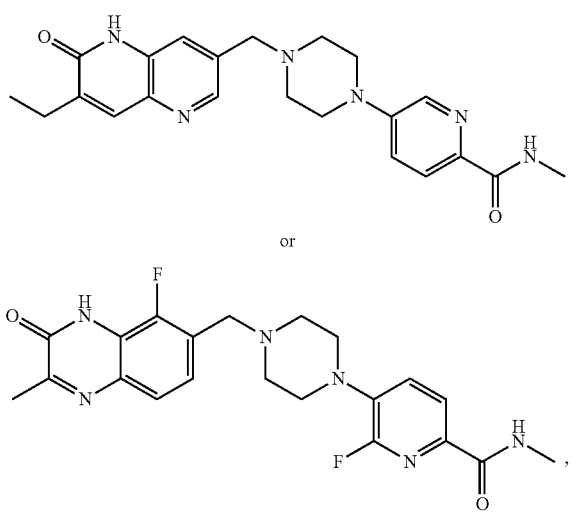

or pharmaceutically acceptable salts thereof.

Embodiment 10. The method of any one of embodiments 1-9, wherein the cancer is a homologous recombinant (HR) deficient cancer.

Embodiment 11. The method of any one of embodiments 1-9, wherein the cancer is characterized by a reduction or absence of BRCA1 and/or BRCA2 gene expression, the absence or mutation of BRCA1 or BRCA2 genes, or reduced function of BRCA1 or 2 proteins.

Embodiment 12. The method of any of embodiments 1-9, wherein the cancer is a solid tumor.

Embodiment 13. The method of any one of embodiments 1-9, wherein the cancer is lymphoma, rhabdoid tumor, multiple myeloma, uterine cancer, gastric cancer, peripheral nervous system cancer, rhabdomyosarcoma, bone cancer, colorectal cancer, mesothelioma, breast cancer, ovarian cancer, lung cancer, fibroblast cancer, central nervous system cancer, urinary tract cancer, upper aerodigestive cancer, leukemia, kidney cancer, skin cancer, esophageal cancer, and pancreatic cancer.

Embodiment 14. The method of any one of embodiments 1-13, wherein the cancer is PARP inhibitor-resistant or has developed resistance to PARP inhibitor therapy.

Embodiment 15. The method of any one of embodiments 1-14, wherein the Polθ inhibitor and the PARP inhibitor are in separate dosage forms.

Embodiment 16. The method of any one of embodiments 1-14, wherein the Polθ inhibitor and the PARP inhibitor are in the same dosage form.

Embodiment 17. A combination comprising a compound of Formula (I) or Formula (II), or a pharmaceutically acceptable salt thereof, and a PARP inhibitor, or a pharmaceutically acceptable salt thereof.

Embodiment 18. The combination of embodiment 17, wherein the PARP inhibitor is Niraparib, Rucaparib, Olaparib, Talazoparib, and Veliparib, AZD5305, or AZD9574, or a pharmaceutically acceptable salt thereof.

Embodiment 19. A compound of Formula (I) or Formula (II) or a pharmaceutically acceptable salt thereof, for use in treating cancer, wherein the compound of Formula (I) or Formula (II) is to be administered simultaneously or sequentially with a PARP inhibitor.

Embodiment 20. The use of embodiment 19, wherein the PARP inhibitor is Niraparib, Rucaparib, Olaparib, Talazoparib, and Veliparib, AZD5305, or AZD9574, or a pharmaceutically acceptable salt thereof.

Embodiment 21. Use of a compound of Formula (I) or Formula (II) in the manufacture of a medicament for treating cancer, wherein the compound of Formula (I) or Formula (II) is to be administered simultaneously or sequentially with a PARP inhibitor.

Embodiment 22. The use of embodiment 21, wherein PARP inhibitor is Niraparib, Rucaparib, Olaparib, Talazoparib, and Veliparib, AZD5303, or AZD9574 or a pharmaceutically acceptable salt thereof.

EXAMPLES

The following examples and references (intermediates) are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: THF=tetrahydrofuran; EtOAc=ethyl acetate; TFA=trifluoroacetic acid; DCM=dichloromethane; DMSO=dimethylsulfoxide; DMF=dimethylformamide; BOC=tert-butoxycarbonyl; TCFH=N,N,N,N'-tetramethylchloroformamidinium hexafluorophosphate; NMI=N-methylimidazole; TBAF=Tetrabutylammonium fluoride; DIBAL-H=Diisobutylaluminum hydride; LDA=Lithium diisopropylamide.

Mass Directed Autopreparative HPLC (MDAP)

Mass directed autopreparative HPLC was used for preparation of the compounds of this invention, and the conditions are given below. The UV detection was an averaged signal from wavelength of 210 nm to 350 nm and mass spectra were recorded on a mass spectrometer using alternate-scan positive and negative mode electrospray ionization.

MDAP Method B

Method B was conducted on a Xselect CSH $C_{18}$ column (typically 150 mm×30 mm i.d. 5 µm packing diameter) at ambient temperature. The solvents employed were:

A=0.1% v/v solution of formic acid in water
B=0.1% v/v solution of formic acid in acetonitrile.
The gradient employed was:

| Time (min) | Flow rate (mL/min) | % A | % B |
|---|---|---|---|
| 0 | 40 | 85 | 15 |
| 1 | 40 | 85 | 15 |
| 10 | 40 | 45 | 55 |
| 10.5 | 40 | 1 | 99 |
| 15 | 40 | 1 | 99 |

MDAP Method C

Method C was conducted on a Xselect CSH Cis column (typically 150 mm×30 mm i.d. 5 µm packing diameter) at ambient temperature. The solvents employed were:

A=0.1% v/v solution of formic acid in water
B=0.1% v/v solution of formic acid in acetonitrile.
The gradient employed was:

| Time (min) | Flow rate (mL/min) | % A | % B |
|---|---|---|---|
| 0 | 40 | 95 | 5 |
| 3 | 40 | 95 | 5 |
| 22 | 40 | 65 | 35 |
| 22.5 | 40 | 1 | 99 |
| 27 | 40 | 1 | 99 |

Synthetic Examples: Compounds of Formula (I)

Example 1

(Z)-(2-((2'-chloro-5'-methoxy-6-methyl-[4,4'-bipyridine]-3-carbonyl)imino)-5-methoxy-1,3,4-thiadiazol-3(2H)-yl)methyl dihydrogen phosphate

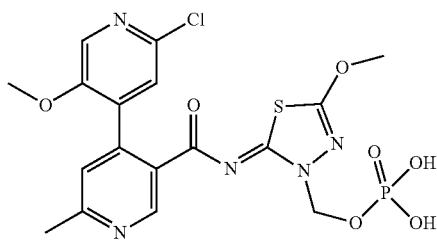 [SMILES: COc1nn(COP(=O)(O)O)/c(=N/C(=O)c2cnc(C)cc2-c2cc(Cl)ncc2OC)s1]

Step 1: 2-chloro-5-methoxypyridin-4-ylboronic acid

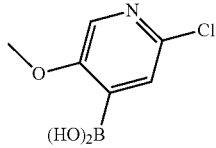

A stirred solution of 2-chloro-5-methoxypyridine (10.0 g, 69.65 mmol) in THF (500 mL) was added LDA (14.9 g, 139.30 mmol) dropwise at −78° C. under N$_2$ atmosphere. The resulting mixture was stirred at −78° C. for 2 h. Then Triisopropyl borate (26.2 g, 139.30 mmol) was added to the above mixture at −78° C. The resulting mixture was stirred at −78° C. for 2 h. Then the resulting mixture was stirred at room temperature for 16 h. The resulting mixture was quenched with HCl (2 N) and stirred at room temperature for 30 min. The resulting mixture was extracted with ethyl acetate. The combined organic layers were washed with brine, dried over anhydrous sodium sulfate, filtered, and concentrated under vacuum. 2-chloro-5-methoxypyridin-4-ylboronic acid (9 g, 68.9%) as a brown solid. MS (ESI) calc'd for (C$_6$H$_7$BClNO$_3$) (M+1)$^+$, 188.0; found 188.0.

Step 2: methyl 2-chloro-5-methoxy-6-methyl-(4,4-bipyridine)-3-carboxylate

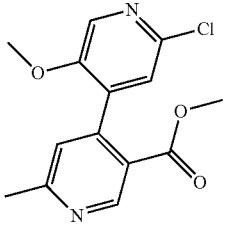

To a degassed solution of methyl 4-chloro-6-methylpyridine-3-carboxylate (700 mg, 3.77 mmol) and 2-chloro-5-methoxypyridin-4-ylboronic acid (918 mg, 4.90 mmol) in dioxane (6 mL) and H$_2$O (2 mL) were added Pd(dppf) Cl$_2$ (275 mg, 0.37 mmol) and K$_2$CO$_3$ (1563 mg, 11.31 mmol) in portions at 80° C. under nitrogen atmosphere. The resulting mixture was stirred at 80° C. for 16 h under nitrogen atmosphere. The resulting mixture was filtered and the filter cake was washed with EtOAc (3×20 mL). The filtrate was concentrated under reduced pressure. The residue was purified by flash column chromatography with 0~60% ethyl acetate in petroleum ether to afford methyl 2-chloro-5-methoxy-6-methyl-(4,4-bipyridine)-3-carboxylate (220 mg, 19.9%) as a white solid. MS (ESI) calc'd for (C$_{14}$H$_{13}$ClN$_2$O$_3$) (M+1)$^+$, 293.1; found 293.1.

Step 3: 2-chloro-5-methoxy-6-methyl-(4,4-bipyridine)-3-carboxylic acid

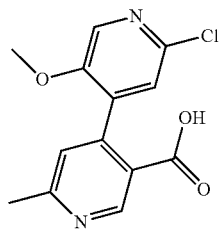 [SMILES: COc1cnc(Cl)cc1-c1cc(C)ncc1C(=O)O]

To a stirred solution of methyl 2-chloro-5-methoxy-6-methyl-(4,4-bipyridine)-3-carboxylate (220 mg, 0.75 mmol) in THF (3 mL) and water (1 mL) were added LiOH·H$_2$O (126 mg, 3.01 mmol). The resulting mixture was stirred at room temperature for 2 h. The mixture was acidified to pH 3 with citric acid. The resulting mixture was extracted with ethyl acetate. The combined organic layers were washed with brine, dried over anhydrous sodium sulfate, filtered, and concentrated under vacuum to afford 2-chloro-5-methoxy-6-methyl-(4,4-bipyridine)-3-carboxylic acid (160 mg, 76.3%) as a white solid. MS (ESI) calc'd for (C$_{13}$H$_{11}$ClN$_2$O$_3$) (M+1)$^+$, 279.0; found, 279.0.

Step 4: 2'-chloro-5'-methoxy-N-(5-methoxy-1,3,4-thiadiazol-2-yl)-6-methyl-(4,4'-bipyridine)-3-carboxamide

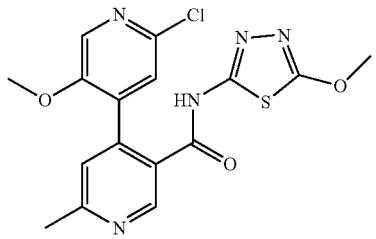

To a solution of 2'-chloro-5'-methoxy-6-methyl-[4,4'-bipyridine]-3-carboxylic acid (50 g, 169 mmol) in MeCN (500 mL) was added 1-methylimidazole (69.2 g, 843 mmol) and 5-methoxy-1,3,4-thiadiazol-2-amine (24.31 g, 185 mmol) in one portion at 25° C. A solution of TCFH (52 g, 185 mmol) in MeCN (500 mL) was added dropwise under nitrogen at 25° C. After being stirred at 25° C. for 4 h, the mixture was filtered and filter cake was washed with a solution of MeCN:water=1:1 (200 mL). The filter cake was dried in vacuo at 45° C. to give 2'-chloro-5'-methoxy-N-(5-methoxy-1,3,4-thiadiazol-2-yl)-6-methyl-(4,4'-bipyridine)-3-carboxamide (57 g, 79% yield adjusted for purity of 96%) as an off-white solid. MS (ESI) calc'd for ($C_{16}H_{14}ClN_5O_3S$) (M+1)$^+$, 392.0, found 392.1. $^1$H NMR (400 MHZ, DMSO-$d_6$) δ 12.93 (s, 1H), 8.81 (s, 1H), 8.17 (s, 1H), 7.55 (s, 1H), 7.44 (s, 1H), 4.08 (s, 3H), 3.63 (s, 3H), 2.59 (s, 3H).

Step 5: (Z)-di-tert-butyl ((2-((2'-chloro-5'-methoxy-6-methyl-[4,4'-bipyridine]-3-carbonyl)imino)-5-methoxy-1,3,4-thiadiazol-3(2H)-yl)methyl)phosphate

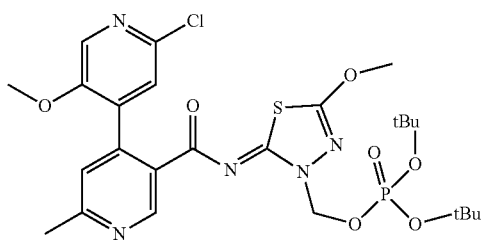 [SMILES: COc1nn(COP(=O)(OC(C)(C)C)OC(C)(C)C)/c(=N/C(=O)c2cnc(C)cc2-c2cc(Cl)ncc2OC)s1]

A mixture of 30 g (77.0 mmol) of 2'-chloro-5'-methoxy-N-(5-methoxy-1,3,4-thiadiazol-2-yl)-6-methyl-[4,4'-bipyridine]-3-carboxamide and 300 mL DMF was cooled to 20° C. To the mixture was added 31.7 g (230 mmol) of $K_2CO_3$, 12.7 g (77.0 mmol) of KI, followed by addition of 39.6 g (153 mmol) of di-tert-butyl (chloromethyl)phosphate over about 10 minutes. The mixture was stirred at 20° C. for 24 h. The reaction was warmed to 25° C., diluted with 300 mL of EtOAc and quenched with 375 ml of water. Layers were separated and the organic layer was washed successively with 300 mL of water and 300 mL of 10 wt/w % aqueous NaCl. After being cooled to 10° C., the solution was treated with 300 mL of heptane over about 3 h. The slurry was stirred overnight, filtered, washed successively with 60 mL of 60% heptane in EtOAc and 2×90 mL of heptane. The wet cake was vacuum dried at 50° C. overnight to afford 27.0 g (57% yield) of (Z)-di-tert-butyl ((2-((2'-chloro-5'-methoxy-6-methyl-[4,4'-bipyridine]-3-carbonyl)imino)-5-methoxy-1,3,4-thiadiazol-3(2H)-yl)methyl)phosphate. as an off-white solid. MS (ESI) calc'd for ($C_{25}H_{33}ClN_5O_7PS$) (M+1)$^+$, 614.2; found 614.2. $^1$H NMR (DMSO-$d_6$, 400 MHz) δ9.29 (s, 1H), 8.14 (s, 1H), 7.42 (s, 1H), 7.29 (s, 1H), 5.85 (br d, 2H, J=10.3 Hz), 4.07 (s, 3H), 3.62 (s, 3H), 2.57 (s, 3H), 1.39 (s, 18H).

Step 6: (Z)-(2-((2'-chloro-5'-methoxy-6-methyl-[4,4'-bipyridine]-3-carbonyl)imino)-5-methoxy-1,3,4-thiadiazol-3(2H)-yl)methyl dihydrogen phosphate

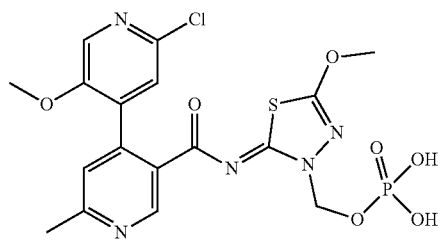 [SMILES: COc1nn(COP(=O)(O)O)/c(=N/C(=O)c2cnc(C)cc2-c2cc(Cl)ncc2OC)s1]

A mixture of 5 g (8.14 mmol) of (Z)-di-tert-butyl ((2-((2'-chloro-5'-methoxy-6-methyl-[4,4'-bipyridine]-3-carbonyl)imino)-5-methoxy-1,3,4-thiadiazol-3(2H)-yl)methyl)phosphate and 20 mL of water was heated to 35° C. To the slurry was added 15 mL (398 mmol) of formic acid over about 10 min. The mixture was stirred for about 4 h, followed by addition of 70 mL of water over about 2 h. After being cooled to 10° C., the slurry was stirred overnight, filtered and washed successively with 2×25 mL of water and 2×25 mL of THF. The wet cake was vacuum dried at 50° C. overnight to afford 3.23 g (79% yield before drying, 72% yield after drying) of (Z)-(2-((2'-chloro-5'-methoxy-6-methyl-[4,4'-bipyridine]-3-carbonyl)imino)-5-methoxy-1,3,4-thiadiazol-3(2H)-yl)methyl dihydrogen phosphate as an off-white solid. MS (ESI) calc'd for ($C_{17}H_{17}ClN_5O_7PS$) (M+1)$^+$, 502.0; found 502.1. $^1$H NMR (DMSO-$d_6$, 400 MHz) δ9.30 (s, 1H), 8.15 (s, 1H), 7.42 (s, 1H), 7.30 (s, 1H), 5.81 (d, 2H, J=9.3 Hz), 4.07 (s, 3H), 3.64 (s, 3H), 2.58 (s, 3H).

Example 2

(Z)-4-((2-((2'-chloro-5'-methoxy-6-methyl-[4,4'-bipyridine]-3-carbonyl)imino)-5-methoxy-1,3,4-thiadiazol-3(2H)-yl)methoxy)-4-oxobutanoic acid

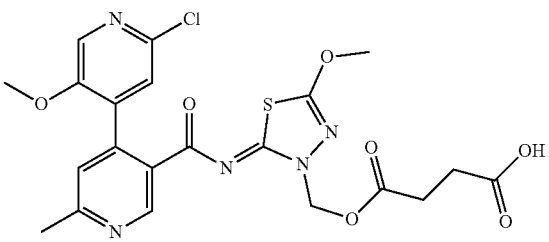 [SMILES: COc1nn(COC(=O)CCC(=O)O)/c(=N/C(=O)c2cnc(C)cc2-c2cc(Cl)ncc2OC)s1]

Step 1: Tert-butyl (chloromethyl) succinate

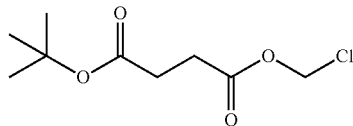

To a solution of 4-(tert-butoxy)-4-oxobutanoic acid (1.507 g, 8.65 mmol) in the solvent mixture of Ethanol (37.5 mL) and Water (5.5 mL) was added cesium carbonate (1.409 g, 4.33 mmol). The mixture was briefly sonicated then stirred for 15 minutes. The solvents were evaporated, and the residue dried overnight under high vacuum.

The dry 4-(tert-butoxy)-4-oxobutanoic acid Cs-salt was dissolved in N,N-Dimethylformamide (DMF) (27.5 mL), bromochloromethane (36.6 mL, 562 mmol) was added and the solution was stirred at room temperature overnight. The precipitate was filtered off and the excess bromochloromethane was evaporated. To the remaining DMF solution 50 mL brine and 50 mL water were added. The mixture was then extracted with EtOAc (40+20+20 mL), the combined organic layer was washed with brine, dried over magnesium sulfate and was evaporated. The crude product was used in the next step without further purification. $^1$H NMR (400 MHZ, DMSO-$d_6$) δ 5.86 (s, 2H), 2.58-2.66 (m, 2H), 2.48-2.53 (m, J=1.70, 1.70, 3.50 Hz, 2H), 1.39 (s, 9H).

Step 2: (Z)-tert-butyl ((2-((2'-chloro-5'-methoxy-6-methyl-[4,4'-bipyridine]-3-carbonyl)imino)-5-methoxy-1,3,4-thiadiazol-3(2H)-yl)methyl) succinate

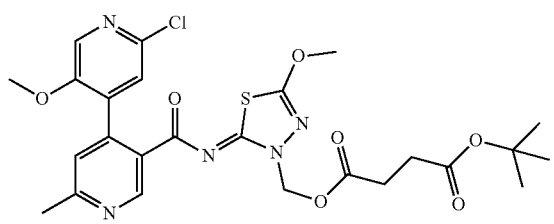 [SMILES: COc1nn(COC(=O)CCC(=O)OC(C)(C)C)/c(=N/C(=O)c2cnc(C)cc2-c2cc(Cl)ncc2OC)s1]

A mixture of 2'-chloro-5'-methoxy-N-(5-methoxy-1,3,4-thiadiazol-2-yl)-6-methyl-[4,4'-bipyridine]-3-carboxamide (250 mg, 0.638 mmol), tert-butyl (chloromethyl) succinate (320 mg, 1.436 mmol), KI (106 mg, 0.638 mmol), and $K_2CO_3$ (265 mg, 1.914 mmol) in N,N-Dimethylformamide (DMF) (5 mL) was stirred at 50° C. for 3 hrs. The mixture was cooled down then 10 mL brine and 10 mL water were added, extracted with EtOAc, the organic layer was washed with brine, dried with sodium sulfate and was evaporated. The residue was purified by silica gel chromatography (12 g Isco RediSep Rf Gold column, eluting with 0-50% (EtOAc/EtOH 3/1) in hexane to afford (Z)-tert-butyl ((2-((2'-chloro-5'-methoxy-6-methyl-[4,4'-bipyridine]-3-carbonyl)imino)-5-methoxy-1,3,4-thiadiazol-3(2H)-yl)methyl) succinate (216 mg, 0.374 mmol, 58.6% yield) as a solid foam. MS (ESI) calc'd for ($C_{25}H_{28}ClN_5O_7S$) (M+1)$^+$, 578.1; found 578.1. $^1$H NMR (DMSO-$d_6$, 400 MHz) δ9.16 (s, 1H), 8.14 (s, 1H), 7.42 (s, 1H), 7.28 (s, 1H), 5.94 (s, 2H), 4.05 (s, 3H), 3.63 (s, 3H), 2.6-2.6 (m, 6H), 2.49 (br s, 1H), 1.34 (s, 9H).

Step 3: (Z)-4-((2-((2'-chloro-5'-methoxy-6-methyl-[4,4'-bipyridine]-3-carbonyl)imino)-5-methoxy-1,3,4-thiadiazol-3(2H)-yl)methoxy)-4-oxobutanoic acid

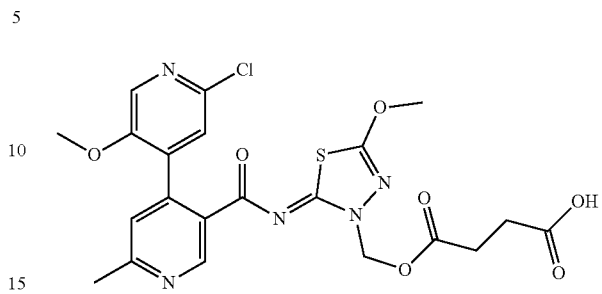

(Z)-tert-butyl ((2-((2'-chloro-5'-methoxy-6-methyl-[4,4'-bipyridine]-3-carbonyl)imino)-5-methoxy-1,3,4-thiadiazol-3(2H)-yl)methyl) succinate (216 mg, 0.374 mmol) was dissolved in Dichloromethane (DCM) (10 mL). TFA (3 mL, 38.9 mmol) was added and the mixture let stand at room temperature for 50 minutes when it was evaporated to dryness. The product was isolated by preparative HPLC (MDAP Method B, TFA) to afford (Z)-4-((2-((2'-chloro-5'-methoxy-6-methyl-[4,4'-bipyridine]-3-carbonyl)imino)-5-methoxy-1,3,4-thiadiazol-3(2H)-yl)methoxy)-4-oxobutanoic acid (136 mg, 0.261 mmol, 69.7% yield) as a white lyophile. The lyophile was crystallized by suspending in 5 mL ether, sonicating for a few minutes then slurring at room temperature overnight. The solid was filtered off and dried to afford 106 mg white crystalline material. MS (ESI) calc'd for ($C_{21}H_{20}ClN_5O_7S$) (M+1)$^+$, 522.1, found 522.1. $^1$H NMR (DMSO-$d_6$, 400 MHZ) δ 9.16 (s, 1H), 8.15 (s, 1H), 7.43 (s, 1H), 7.29 (s, 1H), 5.94 (s, 2H), 4.05 (s, 3H), 3.64 (s, 3H), 3.4-3.5 (m, 1H), 2.6-2.7 (m, 6H), 2.53 (d, 1H, J=4.4 Hz)

Example 3

(Z)-(2-((2'-chloro-5'-methoxy-6-methyl-[4,4'-bipyridine]-3-carbonyl)imino)-5-methoxy-1,3,4-thiadiazol-3(2H)-yl)methyl 2-(piperidin-4-yl)acetate, formic acid salt

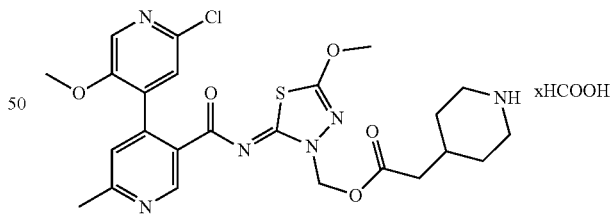

Step 1: Tert-butyl 4-(2-(chloromethoxy)-2-oxoethyl)piperidine-1-carboxylate

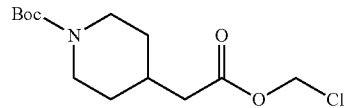 [SMILES: CC(C)(C)OC(=O)N1CCC(CC(=O)OCCl)CC1]

To a solution of 2-(1-(tert-butoxycarbonyl)piperidin-4-yl) acetic acid (1.5 g, 6.04 mmol) in the solvent mixture of ethanol (37.5 mL) and water (5.5 mL) was added cesium carbonate (0.994 g, 3.02 mmol). The mixture was briefly sonicated then stirred for 1 hr. The solvents were evaporated and the residue was dried overnight under high vacuum.

The dry 2-(1-(tert-butoxycarbonyl)piperidin-4-yl)acetic acid Cs-salt was dissolved in N,N-Dimethylformamide (DMF) (27.5 mL) and bromochloromethane (25.5 mL, 393 mmol) was added. The solution was stirred at room temperature overnight. The bromochloromethane excess was evaporated. To the remaining slurry 100 mL icy water was added. The mixture was extracted with EtOAc (30+25 mL), the combined organic layer was washed with brine (1×), dried over Mg-sulfate and was evaporated to afford tert-butyl 4-(2-(chloromethoxy)-2-oxoethyl)piperidine-1-carboxylate (1.735 g, 5.95 mmol, 98% yield) as a pale yellow oil. $^1$H NMR (DMSO-$d_6$, 400 MHz) δ 5.85 (s, 2H), 3.90 (br d, 2H, J=12.2 Hz), 2.37 (d, 2H, J=6.8 Hz), 1.86 (dtd, 1H, J=3.7, 7.6, 15.0 Hz), 1.6-1.7 (m, 2H), 1.3-1.5 (m, 11H), 1.06 (dq, 2H, J=4.4, 12.2 Hz).

Step 2: Tert-butyl (Z)-4-(2-((2-((2'-chloro-5'-methoxy-6-methyl-[4,4'-bipyridine]-3-carbonyl)imino)-5-methoxy-1,3,4-thiadiazol-3(2H)-yl)methoxy)-2-oxoethyl)piperidine-1-carboxylate

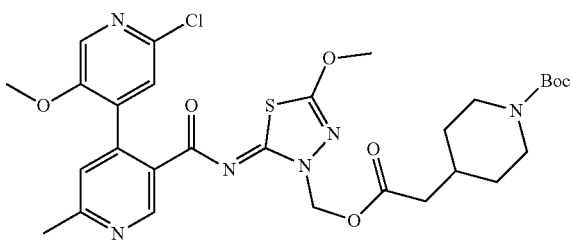 [SMILES: COc1nn(COC(=O)CC2CCN(C(=O)OC(C)(C)C)CC2)/c(=N/C(=O)c2cnc(C)cc2-c2cc(Cl)ncc2OC)s1]

A mixture of 2'-chloro-5'-methoxy-N-(5-methoxy-1,3,4-thiadiazol-2-yl)-6-methyl-[4,4'-bipyridine]-3-carboxamide (100 mg, 0.255 mmol), tert-butyl 4-(2-(chloromethoxy)-2-oxoethyl)piperidine-1-carboxylate (0.124 mL, 0.510 mmol), KI (42.4 mg, 0.255 mmol), and $K_2CO_3$ (106 mg, 0.766 mmol) in N,N-Dimethylformamide (DMF) (2 mL) was heated at 50° C. for 40 minutes. The mixture was diluted with 2 ml. DMF, filtered, and acidified with 50 µL formic acid (FA). The product was isolated by preparative HPLC (MDAP Method C, FA) to afford tert-butyl (Z)-4-(2-((2-((2'-chloro-5'-methoxy-6-methyl-[4,4'-bipyridine]-3-carbonyl)imino)-5-methoxy-1,3,4-thiadiazol-3(2H)-yl)methoxy)-2-oxoethyl)piperidine-1-carboxylate (153 mg, 0.236 mmol, 93% yield). The material was used without further purification in the next step. MS (ESI) calc'd for ($C_{29}H_{35}ClN_6O_7S$) (M+1)$^+$, 647.2, found 647.3.

Step 3: (Z)-(2-((2'-chloro-5'-methoxy-6-methyl-[4,4'-bipyridine]-3-carbonyl)imino)-5-methoxy-1,3,4-thiadiazol-3(2H)-yl)methyl 2-(piperidin-4-yl)acetate, formic acid salt

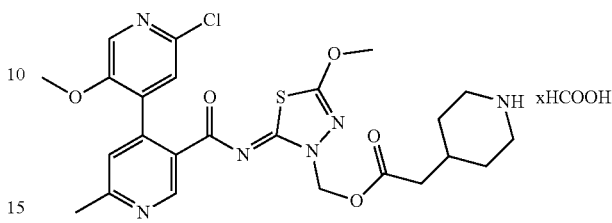

To a solution of tert-butyl (Z)-4-(2-((2-((2'-chloro-5'-methoxy-6-methyl-[4,4'-bipyridine]-3-carbonyl)imino)-5-methoxy-1,3,4-thiadiazol-3(2H)-yl)methoxy)-2-oxoethyl) piperidine-1-carboxylate (150 mg, 0.232 mmol) in Dichloromethane (DCM) (4 mL) was added trifluoroacetic acid (TFA) (4.00 mL) and the mixture was stirred for 15 minutes when it was evaporated. The product was isolated by preparative HPLC (MDAP Method B, FA) to afford (Z)-(2-((2'-chloro-5'-methoxy-6-methyl-[4,4'-bipyridine]-3-carbonyl)imino)-5-methoxy-1,3,4-thiadiazol-3(2H)-yl) methyl 2-(piperidin-4-yl)acetate, formic acid salt (74 mg, 0.125 mmol, 53.8% yield) as a white lyophile. MS (ESI) calc'd for ($C_{24}H_{27}ClN_6O_5S$) (M+1)$^+$, 547.1, found 547.2. $^1$H NMR (DMSO-$d_6$, 400 MHz) δ 9.15 (s, 1H), 8.36 (s, 1H), 8.15 (s, 1H), 7.42 (s, 1H), 7.29 (s, 1H), 5.94 (s, 2H), 4.04 (s, 3H), 3.63 (s, 3H), 3.03 (br d, 2H, J=12.2 Hz), 2.6-2.7 (m, 2H), 2.57 (s, 3H), 2.35 (d, 2H, J=6.8 Hz), 1.8-2.0 (m, 1H), 1.70 (br d, 2H, J=11.7 Hz), 1.1-1.3 (m, 3H).

Biological Examples

1. Hydrolysis Rates of Prodrug (Example 1)

Compound of Example 1 ("Example 1") is a highly soluble phosphate prodrug of the active parent molecule, Compound A. Example 1 is cleaved by alkaline phosphatases on the brush border of the microvilli in the gut and generate Compound A.

Hydrolysis kinetics for Example 1, kcat, Km and kcat/Km, were determined with recombinant human, mouse, and rat alkaline phosphatases from commercial sources using the Invitrogen phosphate sensor protein.

Example 1 was hydrolyzed with similar efficiencies by recombinant human, mouse and rat alkaline phosphatases (Table 2). Three commercially available alkaline phosphatases (APase) were tested for the hydrolysis rate of Example 1. The human and rat enzymes are intestinal alkaline phosphatases, while the mouse APase is a tissue-nonspecific isozyme, which may explain some of the differences in kinetic parameters.

TABLE 2

Comparison of the hydrolysis kinetics of Example 1 in rat, mouse, and human recombinant alkaline phosphatases.

| | Human rAPase | | | Mouse rAPase | | | Rat rAPase | | |
|---|---|---|---|---|---|---|---|---|---|
| Example | kcat ($s^{-1}$) | Km (µM) | kcat/Km (µM$^{-1}$s$^{-1}$) | kcat ($s^{-1}$) | Km (µM) | kcat/Km (µM$^{-1}$s$^{-1}$) | kcat ($s^{-1}$) | Km (µM) | kcat/Km (µM$^{-1}$s$^{-1}$) |
| #1 | 11 | 3.7 | 3.1 | 10 | 3.7 | 2.8 | 14 | 5.2 | 2.7 |
| #2 | 11 | 3.5 | 3.0 | 11 | 4.0 | 2.7 | 15 | 7.8 | 2.0 |

2. Biochemical Activity of Compound A

Compound A is a potent inhibitor of ATPase activity (pIC50=7.8) in the helicase domain of Polθ, as demonstrated using a Polθ ATPase biochemical assay. Consistent with the high sequence homology of Polθ across species, similar inhibition of Polθ was observed with Compound A when tested across species (rat, pIC50=8.0; dog, pIC50=7.8; mouse, pIC50=7.8; monkey, pIC50=7.9). The ATPase activity of Polθ recombinant helicase domain was measured in an enzymatic activity assay. The production of ADP from ATP substrate was determined in a coupled enzyme assay linked to NAD+ production. The NAD+ production was measured by monitoring absorbance changes at 340 nm in a kinetic manner. Gradients of the rate plots were determined for each concentration of Compound A and expressed as % inhibition of enzyme activity. The data shows mean±SD.

Moreover, it was demonstrated that Compound A has >1000-fold selectivity for Polθ vs. Hel308, which share 26% sequence identity and 40% sequence similarity.

3. Cellular Activity of Compound A

The steady state cellular concentration of Compound A was measured in Hela cells after 4 hours exposure to 20 mM Compound A (Table 3). Based on the calculated free fraction of 5.12%, the free cellular concentration of Compound A is calculated to be 3.087 µM (Table 3).

TABLE 3

Intracellular concentration of Compound A measured in HeLa cells.

| Compound | Total cellular concentration (µM) | Fu | Free cellular concentration (µM) |
|---|---|---|---|
| Compound A | 60.308 | 0.0512 | 3.087 |

4. Solubility & PK Assay

The solubility of Compound A in FASSIF (Fasted State Simulated Intestinal Fluid) is 13 ug/mL. The FASSIF solubility for the prodrugs (Examples 1, 2, and 3) is greater than 1000 ug/mL, 72 ug/mL, and 839 ug/mL, respectively.

Pharmacokinetics data of the prodrug compounds of Example 1 and Example 2 and the parent compound (Compound A) were measured. Wistar-Han rats were dosed orally in 1% methyl cellulose formulation with each compound at doses as listed in Table 4 below. Blood samples were collected up to 24 hours and samples were analyzed by LC-MS/MS for Compound A concentration in all three groups.

TABLE 4

| | Dose (mg/kg) | Actual parent dose (mg/kg) | $C_{max}$ parent (µg/mL) | $AUC_{last}$ parent (µg * h/mL) |
|---|---|---|---|---|
| Compound A | 30 | 30 | 6.20 | 79.7 |
| Example 1 | 30.0 | 23.4 | 14.0 | 128.0 |
| Example 2 | 29.9 | 22.5 | 6.78 | 89.0 |

5. Assessment of Combination Synergy Index In Vitro with Compound a and a PARP Inhibitor Cellular efficacy of Compound A, niraparib and the combination of Compound A and niraparib was assessed as % of cell viability in a 7-day CellTiter-Glo® (CTG) assay using the BRCA1 mutant breast cancer line MDA-MB-436 and the BRCA2 mutant ovarian cancer cell line PEO1. Single agent EC50 values for Compound A were above 30 µM in both cell lines.

The synergy between Compound A and niraparib was evaluated in the BRACA1 mutant breast cancer cell line, MDA-MB-436. Cells were treated with an 8×5 drug matrix, with an 8-point, 3-fold dilution ranging from 30 µM to 0.014 µM Compound A, and a 5-point, 3-fold dilution ranging from 100 nM to 1.2 nM Niraparib. After 7 days, cell viability was assessed with the CTG assay. Dose response curves were interpolated using GraphPad Prism 9ART, and the synergy of drug combinations using data from the cell viability assays was analyzed with ComBenefit 2.02 (Table 4). Synergy scores of Compound A and Niraparib co-treatment were calculated using Combenefit. Synergy scores for combination matrices calculated with the Bliss, HAS (least stringent) and Loewe (most stringent) models are shown. The results showed that Niraparib synergizes with Compound A and decreases the EC50 values of Compound A in MDA-MB-436 cells.

Using the same experimental setup, the synergy between Compound A and niraparib was also evaluated in PEO1 cells, a BRCA2 mutant ovarian cancer cell line. Dose response curves were interpolated using GraphPad Prism 9 (FIG. 4A), and the synergy of drug combinations was analyzed with ComBenefit 2.02 (Table 4). The results showed that Niraparib synergizes with Compound A and decreases the $EC_{50}$ values of Compound A in PEO1 cells.

TABLE 4

Compound A EC50 values in combination with the indicated Niraparib concentration.

| Compound A | Niraparib (nM) | | | | | Synergy score (ComBenefit) | | |
|---|---|---|---|---|---|---|---|---|
| EC50 (nM) | 0 | 3 | 10 | 30 | 100 | Loewe | Bliss | HAS |
| MDA-MB-436 | >30 | n/a | 596 | 189 | 162 | 19 | 8 | 19 |
| PEO1 | >30 | 250 | 79 | 58 | n/a | 36 | 20 | 38 |

Screening of additional cell lines confirmed the synergistic effects of Compound A and Niraparib combination in several Homologous Recombination-deficient (HR-D) in vitro models, summarized in Table 5.

TABLE 5

Summary of the HR-D cell lines that showed Compound A and Niraparib combination efficacy.

| Cell line | Lineage | HR status | Comb Benefit | Assay Format |
|---|---|---|---|---|
| PEO1 | Ovary | BRCA2-mut. pTyr1655Ter | Yes | 7 days CTG |
| DoTc2-4510 | Cervical | BRCA2-mut. pR3128 | Yes | 10 days nuclear count viability |
| MDA-MB-436 | Breast | BRCA1-Homo mut. 5396 + 1G > A | Yes | 7 days CTG |
| SNU601 | Gastric | Rad51 methylated promoter | Yes | 7 days nuclear count viability |
| DLD1 BRCA2 KO | Colorectal | BRCA2 KO | Yes | 14 days CFA |

The synergy between ART558 and niraparib was evaluated in MDA-MB-436 cells. See Table 6.

TABLE 6

$EC_{50}$ of ART558 and niraparib combination in MDA-MB-436 cells.

| MDA-MB-436 $EC_{50}$ (nM) of Artios' | Niraparib (nM) | | | |
|---|---|---|---|---|
| POLQi | 0 | 10 | 30 | 100 |
| ART558 | >100,000 | 3,985 | 1,758 | 1,023 |

Synergistic effects of Compound A and ART558 were confirmed with talazoparib. See Table 7.

TABLE 7

$EC_{50}$ of Compound A or ART558 in combination with Talazoparib in MDA-MB-436 cells.

| MIDA-MB-436 | Talazoparib (nM) | | | | Synergy score (ComBenefit) | | |
|---|---|---|---|---|---|---|---|
| $EC_{50}$ (nM) | 0 | 1.2 | 3.7 | 10 | Loewe | Bliss | HAS |
| Compound A | >30,000 | 95 | 319 | 803 | 14 | 19 | 14 |
| ART558 | >30,000 | 2,295 | 1,087 | n/a | 16 | 7 | 18 |

6. Efficacy Study of Compound a in HR Deficient Human Cell Line Xenograft Model MDA-MB-436

The effect of Compound A on tumor growth in vivo was assessed in mice bearing BRCA1 mutant MDA-MB-436 cell line xenografts. Ten million ($10e^7$) MDA-MB-436 viable cells were implanted with 50% Matrigel in the flank of the 5-7 weeks old female NSG mice (Jax). When the tumor volume reach to around 200 $mm^3$ size, the animals were randomized into efficacy study. MDA-MB-436 tumor bearing animals were either dosed twice daily with vehicle (0.5% Methylcellulose) BID, PO or Compound A 10 mg/kg BID or 30 mg/kg BID, PO alone or in combination with Niraparib 35 mg/kg QD, PO.

The effect of Compound A on tumor growth in vivo was assessed in 5-7 weeks old female NSG mice bearing BRCA1 mutant MDA-MB-436 CDX model. Compound A at 30 mg/kg BID PO dose induced a significant but modest 24% tumor growth inhibition (p<0.05). Niraparib at 35 mg/kg QD dose also induced a significant tumor volume change compared to vehicle 72% TGI at day 43 (p<0.05). When niraparib was dosed in combination with Compound A BID either at 10 mg/kg and 30 mg/kg dose, complete tumor regression was observed (FIG. 1). These in vivo studies suggest Compound A is synergistic in combination with niraparib in HR deficient TNBC CDX model.

Figure 2:
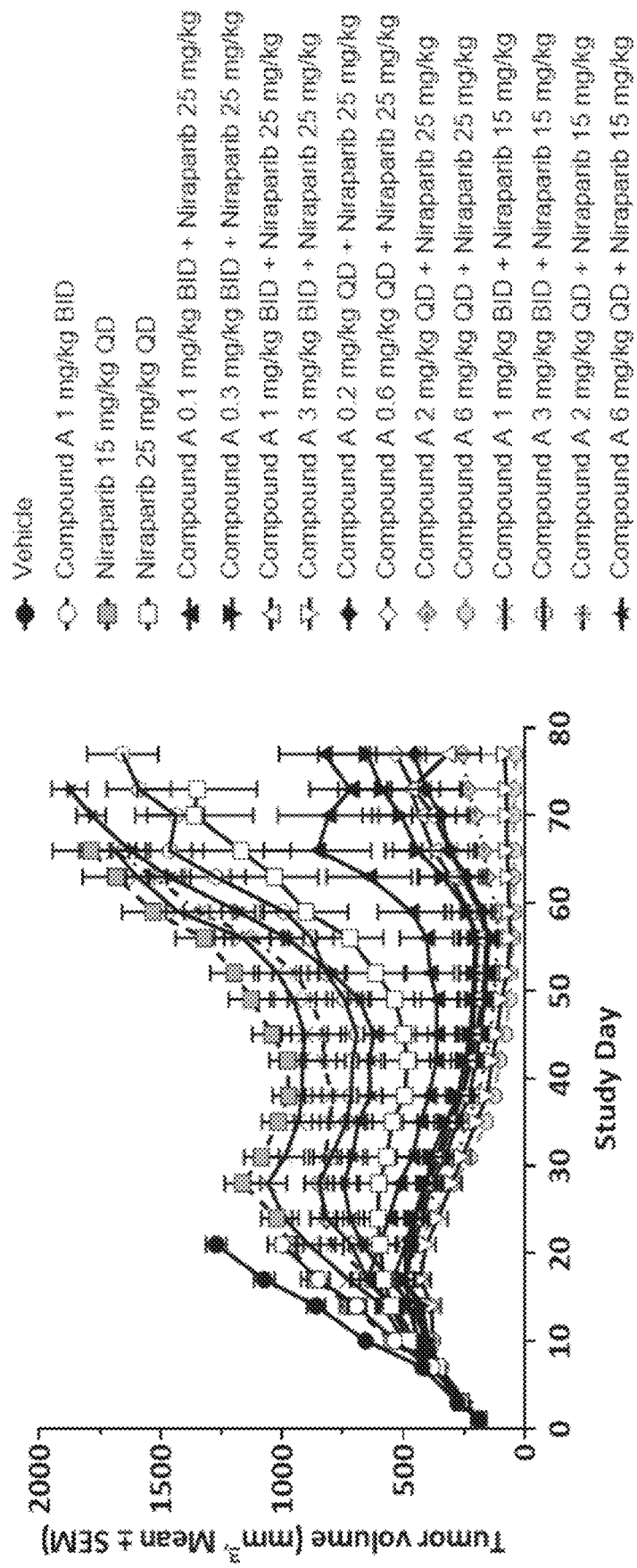
FIG. 2 displays an efficacy study of Compound A in BRCA1 mutant MDA-MB-436 model.

To explore the lowest efficacious dose of Compound A with clinically relevant niraparib 25 mg/kg (corresponding 200 mg clinical dose), the efficacy of BID and QD regimen of compound A was evaluated ranging from 0.2 mg/kg to 6 mg/kg study. There was limited monotherapy response to 1 mg/kg BID dose of compound A, whereas niraparib at QD 25 mg/kg dose delayed tumor growth about 40 days compared to vehicle (Tumor volume to reach 1200 $mm^3$ 21 days Vehicle Vs 61 days Niraparib) (FIG. 2). The combination of 25 mg/kg niraparib and compound A administered at 0.1, 0.3, 1, or 3 mg/kg BID produced tumor regression in 10, 30, 50, and 90% of mice, respectively. The combination of 25 mg/kg niraparib and compound A administered at 0.2, 0.6, 2, or 6 mg/kg QD produced tumor regressions in 20, 20, 80, and 100% of mice, respectively. Compound A administered at 1 mg/kg BID with 25 mg/kg niraparib resulted in tumor regression in 50% of mice. The frequency of tumor regressions was enhanced by escalating doses of compound A (FIG. 2).

7. Efficacy Study of Compound a in a BRCA Mutant Ovarian PDX Model

An in vivo efficacy study was conducted using a HR-deficient (BRCA1 Frame shift (FS) mutation) PARP-inhibitor progressed ovarian carcinoma patient-derived xenograft (PDX) model 134-T.

Figure 3:
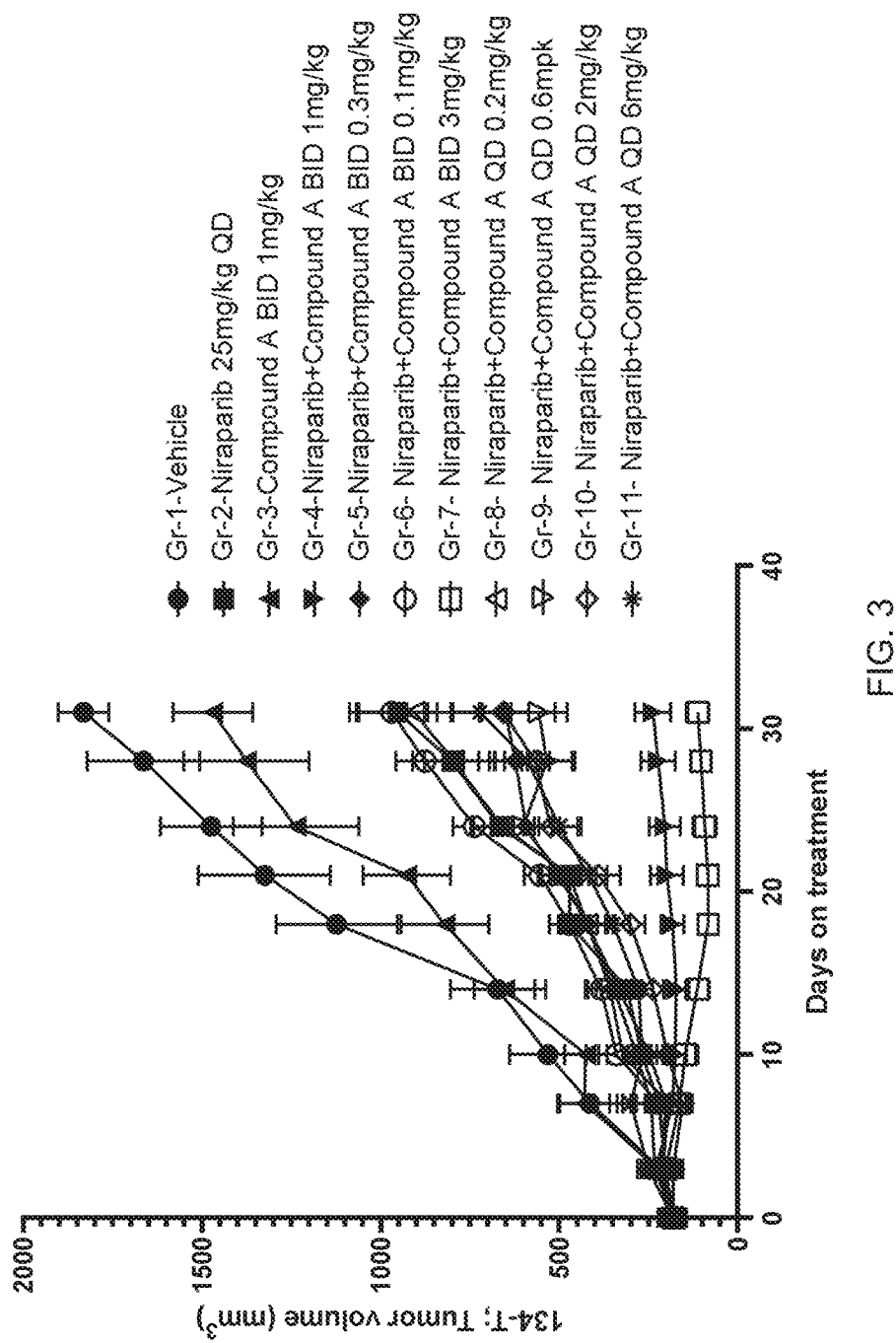
FIG. 3 displays an efficacy study of Compound A in 134-T PDX model. Mixed effects model with Tukey test was applied to calculate statistics, *p<0.05 after adjustment for multiplicity.

Female NOD SCID gamma (NSG) mice were implanted with 4 mm×4 mm fragments of the HR-deficient (BRCA1 mut) 134-T ovarian cancer PDX model and when average tumor volume was around 150 mm$^3$, animals were randomized and treated either with niraparib (25 mg/kg QD) or compound A at BID doses of 1 mg/kg or in combination with Niraparib 25 mg/kg and doses of compound A ranging from 0.1 mg/kg BID to 6 mg/kg. There was no significant monotherapy response to 1 mg/kg BID dose of Compound A. (p=0.77) whereas niraparib alone at 25 mg/kg QD resulted in 58% tumor growth inhibition (p=0.005) (FIG. 3). Both BID dosing of 1 mg/kg and 3 mg/kg compound A with niraparib resulted in statistically significance in tumor volume at day 28 compared to both vehicle and niraparib (TGI % 97 and 105, respectively) (p=0.03 for both) (FIG. 3).

Figure 4:
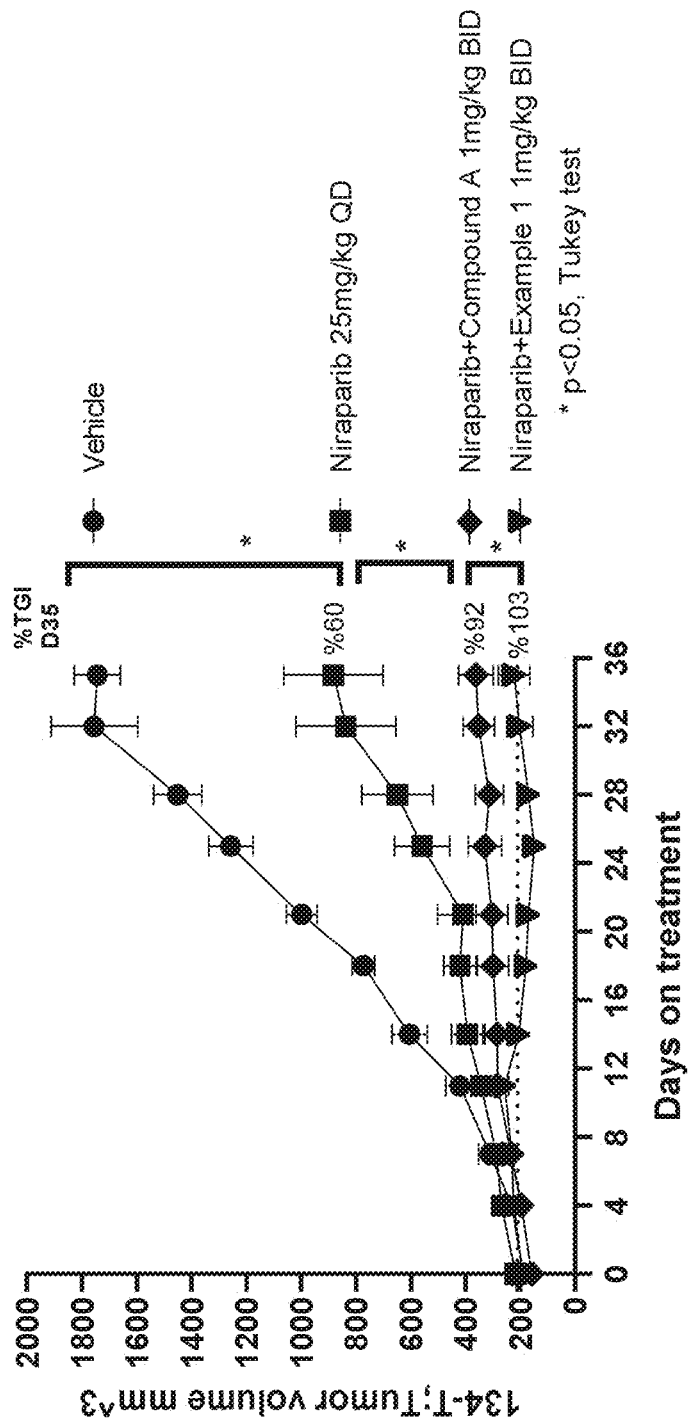
FIG. 4 displays an efficacy study of Compound A and prodrug Example 1 in 134-T PDX model. Mixed effects model with Tukey test was applied to calculate statistics, *p<0.05 after adjustment for multiplicity.

8. Efficacy Study of Prodrug Example 1 and Compound a in a BRCA Mutant Ovarian PDX Model The effect of prodrug Example 1 and Compound A on tumor growth was assessed in mice bearing Ovarian PDX model 134-T model. Niraparib at 25 mg/kg QD dose led to significant difference in tumor volume compared to vehicle (TGI 60%, p<0.0001) and 1 mg/kg BID dose of compound A in combination with niraparib led to significant tumor volume difference compared to vehicle and niraparib with TGI 92% (p<0.001) (FIG. 4). And 1 mg/kg BID dose of Example 1 as niraparib combination demonstrated statistically significant difference in tumor volume compared to vehicle and niraparib with TGI at 103% (p<0.001) (FIG. 4). These results suggests prodrug Example 1 demonstrated robust combination efficacy with niraparib in 134-T HR deficient PDX model.

9. Efficacy Study of Prodrug Example 1 in MDA-MB-436 TNBC CDX Model

The efficacy of prodrug Example 1 in combination with niraparib, olaparib in TNBC MDA-MB 436 CDX model Ten million (10e$^7$) MDA-MB-436 viable cells were implanted with 50% Matrigel in the back flank of the 5-7 weeks old NSG mice (Jax). When the tumor volume reach to around 200 mm$^3$ size, the animals were randomized into efficacy study MDA-MB-436 tumor bearing animals were either dosed twice daily with vehicle 0.5% Methylcellulose BID, PO or Example 1 mg/kg BID or 2 mg/kg QD, PO alone or in combination with Niraparib 25 mg/kg QD, PO or Olaparib 100 mg/kg QD, PO for 42 days.

Figure 5:
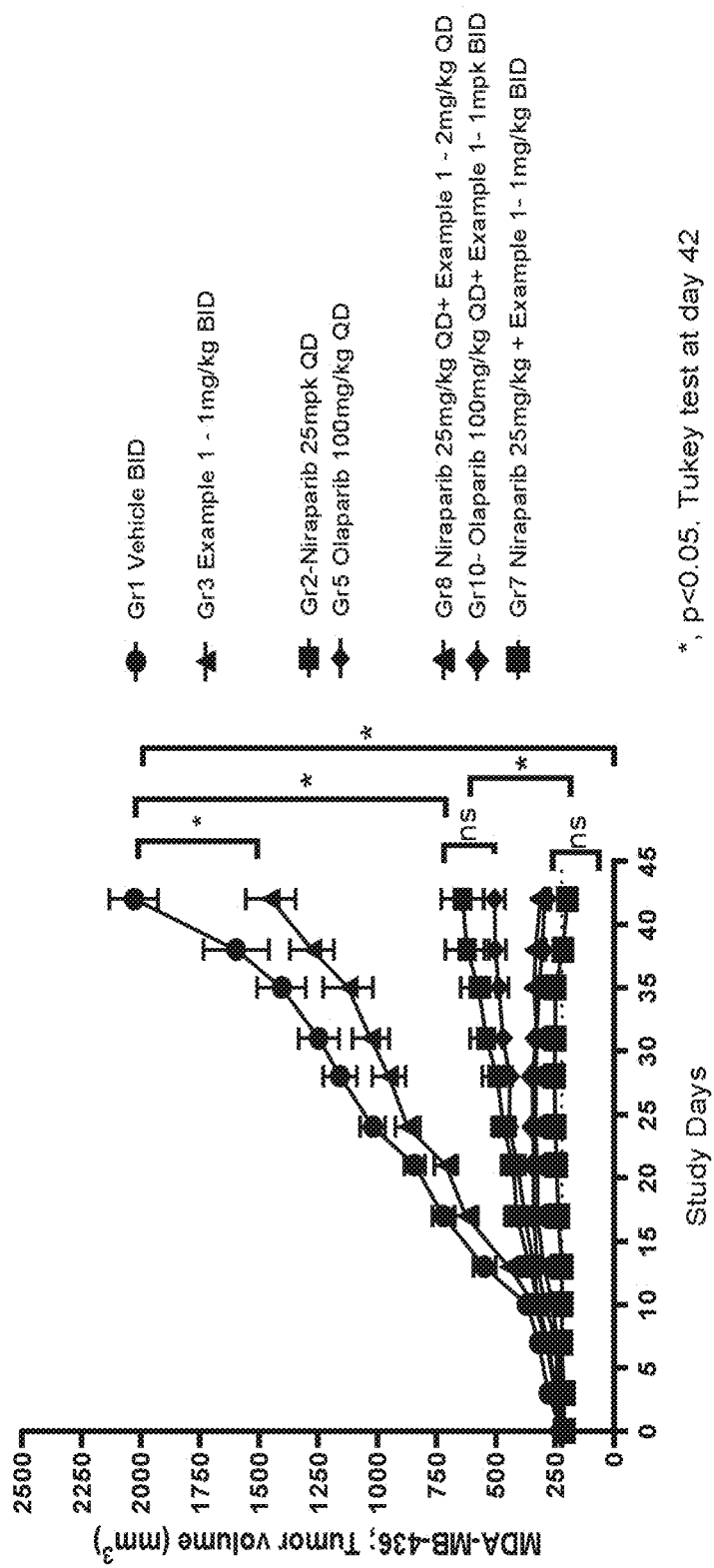
FIG. 5 displays an efficacy study of prodrug Example 1 in BRCA1 mutant TNBC MDA-MB-436 CDX model. Mixed effects model with Tukey test was applied to calculate statistics, *p<0.05 after adjustment for multiplicity.

Example 1 at 1 mg/kg BID induced a significant but modest monotherapy 31% tumor growth inhibition compared to vehicle at day 42 (p=0.0371) and niraparib alone at 25 mg/kg QD induced 76% tumor growth inhibition (p<0.0001) and olaparib alone at 100 mg/kg QD dose induced 84% tumor growth inhibition (p<0.0001) compared to vehicle at day 42 (FIG. 5). Both BID dosing of 1 mg/kg and QD dosing of 2 mg/kg Example 1 induced statistically significant difference in tumor volume at day 42 compared to vehicle (TGI % 101 and % 94, respectively with p<0.0001) and compared to niraparib as well (p=0.00233) at Day 42. BID dosing of 1 mg/kg Example 1 in combination with olaparib induced significant tumor volume difference with 96% TGI at day 42 compared to vehicle (p<0.0001) and olaparib (p=0.002) (FIG. 5).

The efficacy of the combination of prodrug Example 1 and niraparib was also studied in an Homologous recombination (HR)-deficient (BRCA2 mutant) ovarian cancer cell line xenograft CDX PEO1 model and in an HR-deficient (BRCA1 mutant) 134-T ovarian cancer PDX. In both studies, BID dosing of 1 mg/kg Example 1 in combination with niraparib induced statistically significant difference in tumor volume compared to vehicle and compared to niraparib.

10. Re-Sensitization of 134-T PDX Tumors Progressing on Niraparib

Figure 6:
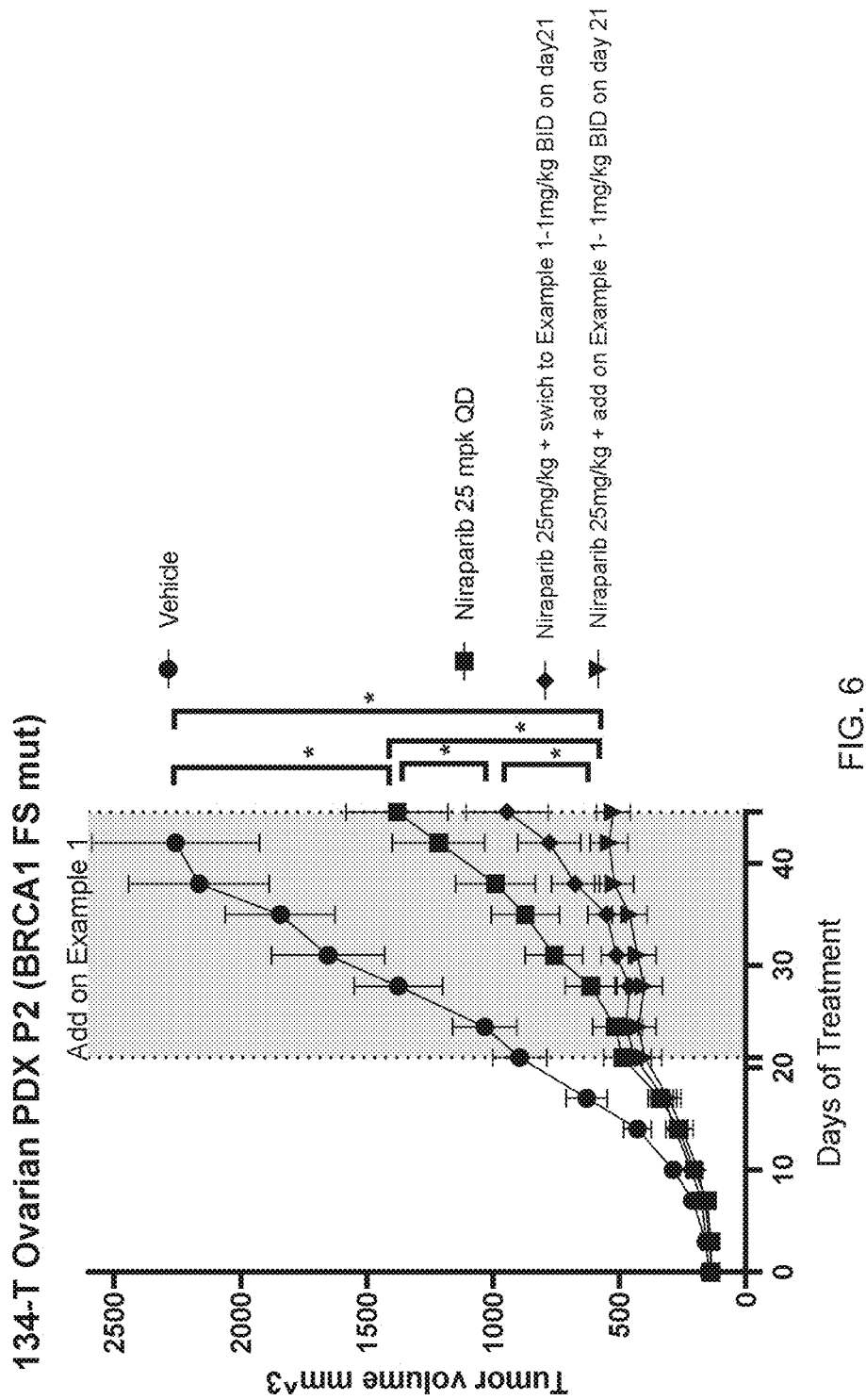
FIG. 6 displays an efficacy study showing that prodrug Example 1 may re-sensitize 134-T PDX tumors progressing on Niraparib. Mixed effects model with Tukey test was applied to calculate statistics, *p<0.05 after adjustment for multiplicity.

134-T PDX tumor bearing animals were treated either with vehicle or Niraparib 25 mg/kg QD. Vehicle treated animals reached the maximum allowed tumor volume at day 42 and Niraparib treatment slowly progressed (FIG. 6). On day 21 when the average tumor volume reached to 500 mm$^3$, the Niraparib dosed animals were randomized into three groups: one group continued receiving Niraparib 25 mg/kg only; second group switched to POLQ inhibitor Example 1 at 1 mg/kg BID dose; and third group received combination of Niraparib 25 mg/kg and Example 1 at 1 mg/kg BID dose. Niraparib only receiving tumors further progressed and reached to ~1400 mm$^3$ size at day 45 and, while the single agent Example 1 arms slowly grew and reached to 945 mm$^3$. And the combination arm with niraparib and Example 1 at 1 mg/kg BID significantly controlled disease progression, with an average tumor volume of 525 mm$^3$. This data suggests that inhibiting POLQ may re-sensitize tumors progressing on PARP inhibitors.

The efficacy of the combination of Example 1 and niraparib is to be studied in PARP inhibitor-resistant ovarian PDX models. See Parmar et al., "The CHK1 Inhibitor Prexasertib Exhibits Monotherapy Activity in High-Grade Serous Ovarian Cancer Models and Sensitizes to PARP Inhibition," Clin Cancer Res; 25 (20), 6127-6140 (2019).

11. Efficacy Study in DLD1 BRCA2-Deleted CDX Model

The efficacy of Compound A or Niraparib as monotherapies as well as for the combination of Compound A and Niraparib was studied in the BRCA2 deleted model DLD1 (DLD1 BRCA2$^{del}$) Furthermore, the studies examined the durability and response rate for the combination of Compound A and Niraparib. The efficacy of each treatment group was compared to the vehicle control group or Niraparib administered alone at 35 mg/kg QD (once per day). In addition, the efficacy of the treatment response for the combination groups were compared to Niraparib alone.

Figure 7:
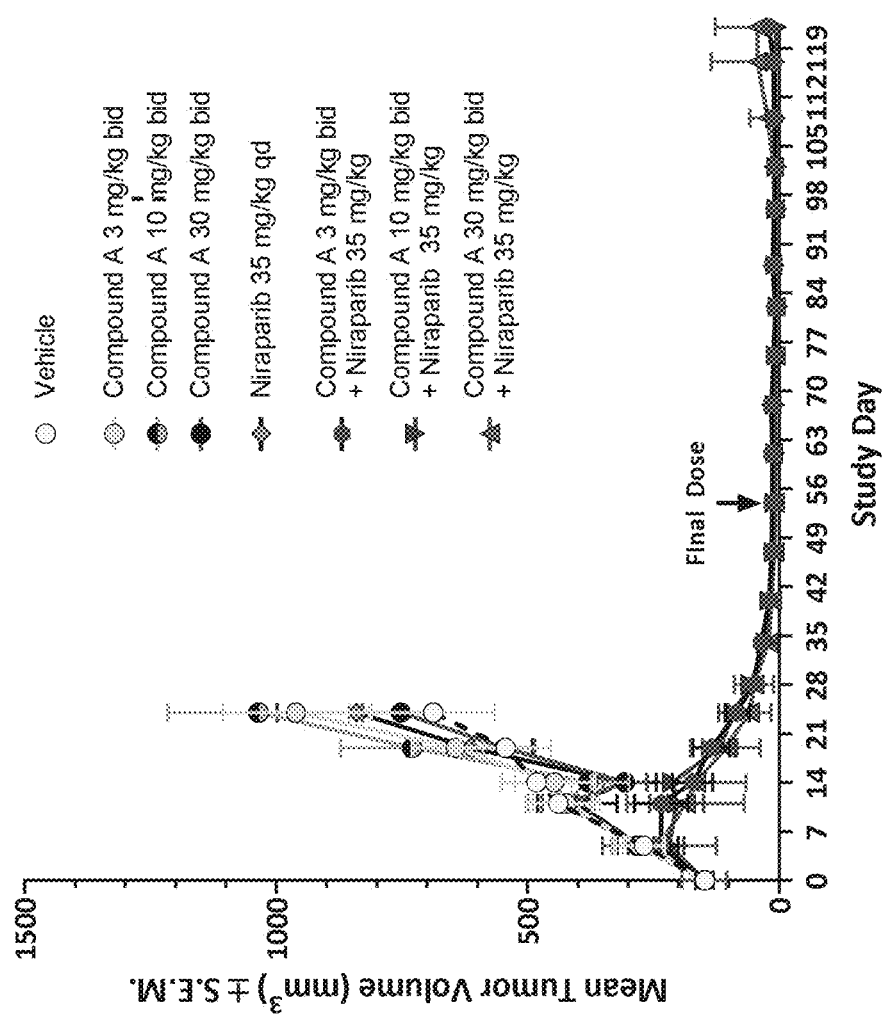
FIG. 7 displays an efficacy study of Compound A in DLD1 BRCA2-deleted CDX Model.

DLD1 BRCA2$^{del}$ Cells were expanded in RPMI with 10% fetal bovine serum. Mean TV at dosing start was approximately 148 mm$^3$, with seven mice randomized to each treatment group. The study consisted of eight treatment groups. The treatment groups on day 24 were compared to the control group on day 24 to calculate the TGI. Compound A administered at 3 mg/kg, 10 mg/kg, or 30 mg/kg BID produced −50%, −64%, and −12% TGI, respectively. Niraparib produced −12% TGI. The combination of 35 mg/kg QD Niraparib and Compound A administered at 3 mg/kg, 10 mg/kg, or 30 mg/kg produced mean TGI of 112%, 111%, and 117% TGI, respectively. The vehicle, Compound A and Niraparib monotherapy groups were terminated on day 24 and the study continued for the Compound A with Niraparib combination groups. All treatments were discontinued on day 54, and the tumor regrowth as assessed until day 122. The combination groups did not progress off treatment (see FIG. 7). The combination of Compound A with Niraparib enriched for complete responses and tumor regressions and the response was maintained during the observation period.

12. Efficacy Study in HR Deficient Human Cell Line Xenograft Model MDA-MB-436

The effect of Example 1 on tumor growth in vivo was assessed in female NOD SCID mice, 6-8 weeks of age, bearing BRCA1 mutant MDA-MB-436 CDX model.

Ten mice were assigned to each treatment group within the efficacy study. The study consisted of four treatment groups. Mice were dosed orally with Vehicle A, BID (the vehicle for example 1; 1% 400 cps methylcellulose in sterile water) and Vehicle B, QD, (the vehicle for niraparib, 0.5% 400 cps methylcellulose in sterile water) (Group 1), Example 1 at 1 mg/kg BID (Group 2), niraparib at 25 mg/kg QD (Group 3), and niraparib at 25 mg/kg QD in combination with Example 1 at 1 mg/kg BID (Group 4).

The duration for the vehicle and Example 1 treatment group was 29 days or earlier if the TV endpoint criteria was met. TV endpoint for individual treatment groups was defined as 50% of mice within the treatment group currently or previously contained tumors greater than 2000 mm³. If an individual mouse reached endpoint prior to the group, it was euthanized, and the remainder of the mice continued until endpoint criteria for the group was reached.

Figure 8:
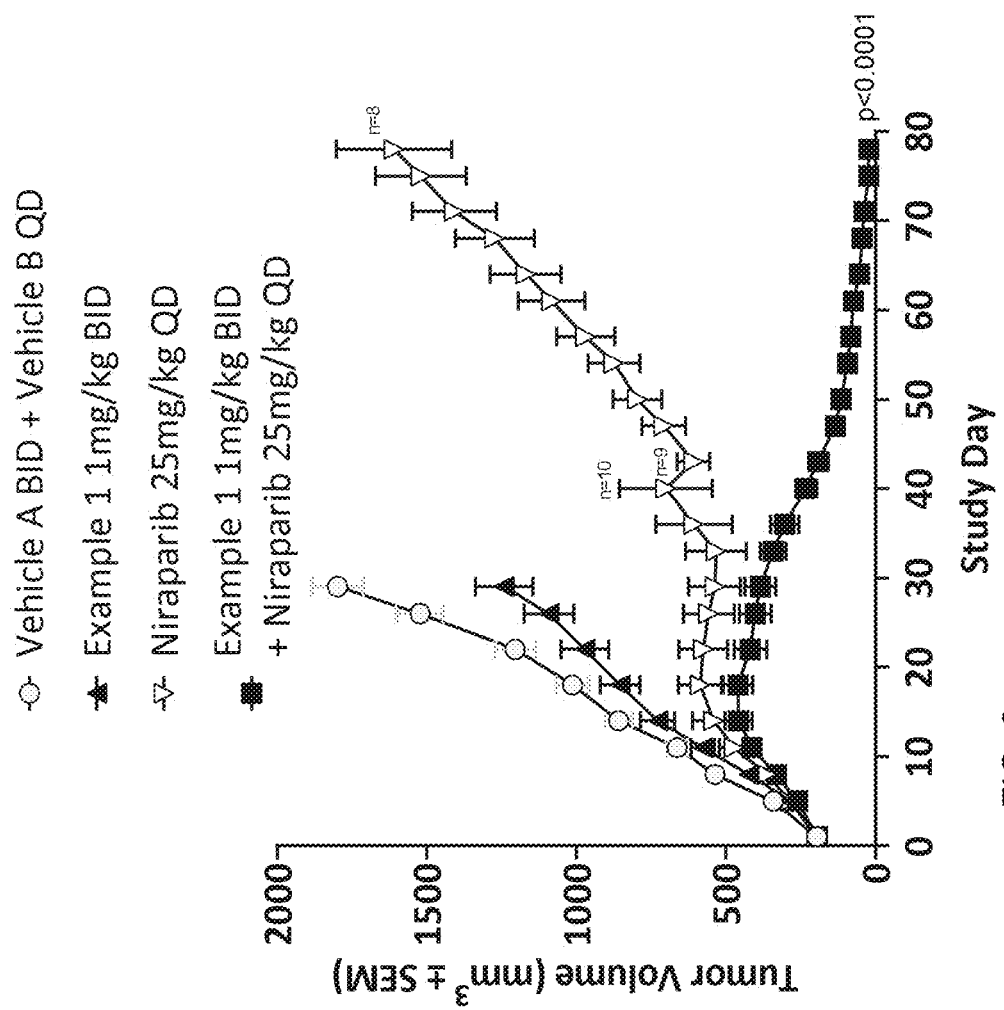
FIG. 8 displays an efficacy study of prodrug Example 1 in HR deficient human cell line xenograft model MDA-MB-436. Statistical analysis performed using Mixed-effects model with Sidak multiple comparisons test.

The vehicle control group reached endpoint TV on study day 29, and on day 30 both groups 1 and 2 were euthanized. The study continued for groups 3 and 4 until study day 78. FIG. 8 presents the mean TV, which only includes mice that remained in the study on the days of measurement. Mice were euthanized when they reached the TV endpoint, or on day 78, whichever occurred first. There was no significant body weight loss observed at any time during the study.

Compared to the vehicle group, each treatment group produced statistically significant TGI. Example 1, niraparib, and the combination produced 35%, 79%, and 88% TGI, respectively. On day 78, the efficacy for the combination of Example 1 and niraparib was compared to that of niraparib alone. The combination of niraparib and Example 1 produced a mean TV of 23.7 mm³ and all tumors were responding by 100% tumor regressions. In addition to tumor regression, complete responses were also observed in 70% of mice.

13. Efficacy Study in 031-T Ovarian PDX Tumors Progressing on Niraparib

An in vivo efficacy study was conducted using an HR-deficient (BRCA nonsense mutation) carboplatin progressed ovarian carcinoma patient-derived xenograft (PDX) model 031-T.

Figure 9:
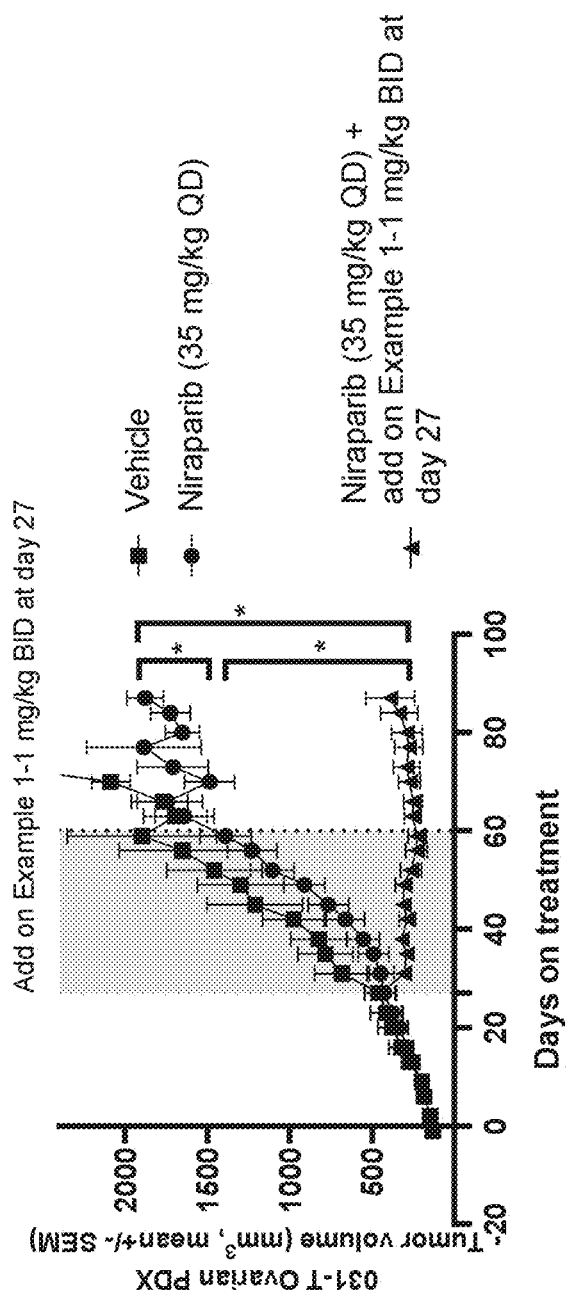
FIG. 9 displays an efficacy study of prodrug Example 1 in 031-T Ovarian PDX tumors progressing on Niraparib. Mixed effects model with Tukey test was applied to calculate statistics, n=4, *p<0.05 after adjustment for multiplicity.

Female NOD SCID gamma (NSG) mice were implanted with 4 mm×4 mm fragments of the HR-deficient (BRCA1 mut) 031-T ovarian cancer PDX model and when average tumor volume was around 100 mm³, animals were randomized and treated either with vehicle or niraparib (35 mg/kg QD). The tumors did not respond to niraparib 35 mg/kg QD and progressed within 27 days. On day 27, when the average tumor volume reached to 500 mm³, the Niraparib dosed animals were randomized into two groups: one group continued receiving Niraparib 35 mg/kg, QD only; second group received combination of Niraparib 35 mg/kg, QD and Example 1 at 1 mg/kg BID dose (n=4). Both vehicle and Niraparib only receiving tumors further progressed and reached to ~2000 mm³ size at day 59, while the combination arm with niraparib and Example 1 at 1 mg/kg BID significantly delays disease progression, with an average tumor volume of 230 mm³ (TGI 123% compared to day 27 with 27% tumor regression) (FIG. 9). This data suggests that addition of POLQ inhibitor delays tumor progression on PARP inhibitors, while niraparib monotherapy results in continuous tumor growth.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound of Formula (I):

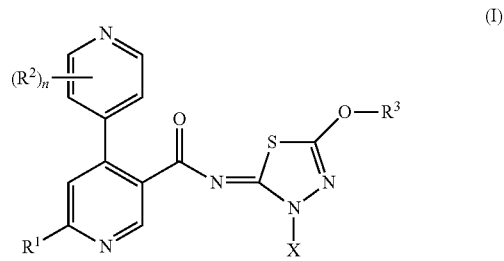

wherein:
$R^1$ is H, halo, $C_{1-4}$ alkyl, $C_{1-4}$ alkoxy, $C_{1-4}$ haloalkyl, or $C_{1-4}$ haloalkoxy;
each $R^2$ is independently halo, $C_{1-4}$ alkyl, $C_{1-4}$ haloalkyl, $C_{1-4}$ alkoxy, or $C_{1-4}$ haloalkoxy;
X is a prodrug moiety;
$R^3$ is $C_{1-4}$ alkyl, $C_{1-4}$ haloalkyl, $C_{3-6}$ cycloalkyl, or heterocycloalkyl, wherein said $C_{3-6}$ cycloalkyl and said heterocycloalkyl are optionally substituted with 1 to 4 $R^{3a}$ substituents, each of which is independently selected from halo, $C_{1-4}$ alkyl, $C_{1-4}$ haloalkyl, $C_{1-4}$ haloalkoxy, -$L^3$-O—$C_{1-4}$ alkyl, -$L^3$-OH, and oxo;
each $L^3$ is independently selected from a bond and $C_{1-4}$ alkylene;
each heterocycloalkyl has from 4 to 6 ring members and from 1 to 3 heteroatoms as ring vertices independently selected from N, O, and S; and
n is 0, 1, 2, or 3;
or a pharmaceutically acceptable salt thereof.

2. The compound of claim 1, or a pharmaceutically acceptable salt thereof, wherein X is —CH($R^c$)—O—P(O)(O$R^a$)(O$R^b$), —CH($R^c$)—O—C(O)—$C_{1-6}$ alkylene-CO$_2$H, —CH($R^c$)—O—C(O)—$C_{1-6}$ alkylene-O—P(O)(O$R^a$)(O$R^b$), —CH($R^c$)—O—C(O)—$C_{1-6}$ alkylene-P(O)(O$R^a$)(O$R^b$), —CH($R^c$)—O—C(O)—$C_{1-6}$ alkylene-N$R^a R^b$, or —CH($R^c$)—O—C(O)—$C_{1-6}$ alkylene-heterocycloalkyl, and wherein $R^a$ and $R^b$ are each independently H or $C_{1-4}$ alkyl, and $R^c$ is independently selected from hydrogen and methyl.

3. The compound of claim 1, or a pharmaceutically acceptable salt thereof, wherein X is

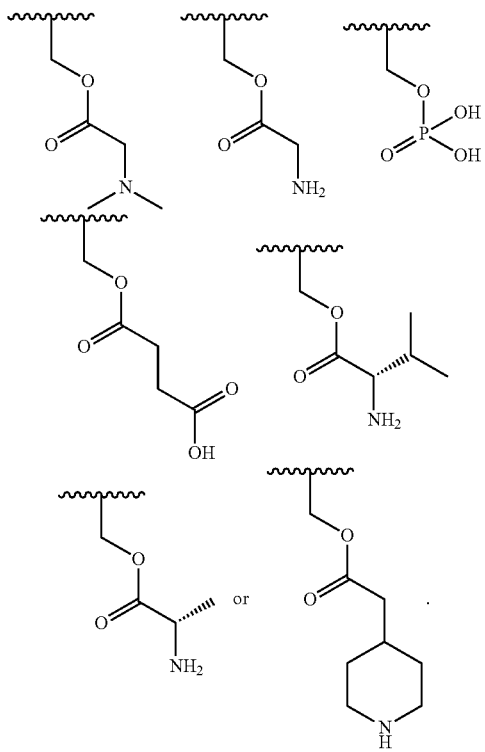

4. The compound of claim 1, or a pharmaceutically acceptable salt thereof, wherein X is

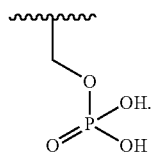 [SMILES: *COP(=O)(O)O]

5. The compound of claim 1, or a pharmaceutically acceptable salt thereof, wherein $R^1$ is $C_{1-4}$ alkyl.

6. The compound of claim 1, or a pharmaceutically acceptable salt thereof, wherein each $R^2$ is independently halo, $C_{1-4}$ alkoxy, or $C_{1-4}$ haloalkoxy.

7. The compound of claim 1, or a pharmaceutically acceptable salt thereof, wherein n is 1, 2, or 3.

8. The compound of claim 1, or a pharmaceutically acceptable salt thereof, wherein $R^3$ is $C_{1-4}$ alkyl or $C_{1-4}$ haloalkyl.

9. A pharmaceutical composition comprising a compound of claim 1, and at least one pharmaceutically acceptable excipient.

10. The compound of claim 1, having the structure:

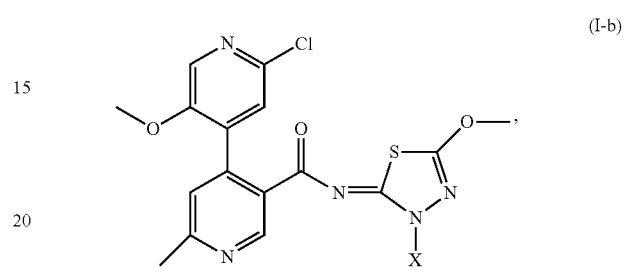

(I-b)

or a pharmaceutically acceptable salt thereof.

11. A compound having the structure:

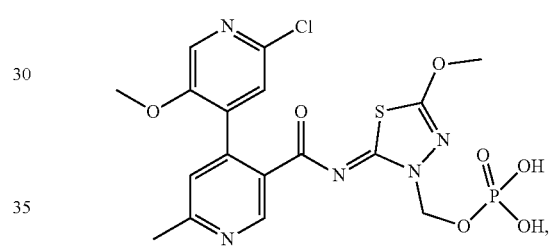

or a pharmaceutically acceptable salt thereof.

12. A compound having the structure:

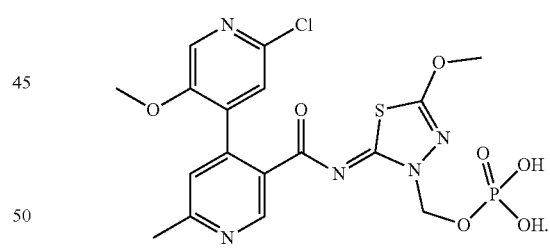

13. A pharmaceutical composition comprising a compound of claim 11 or a pharmaceutically acceptable salt thereof, and at least one pharmaceutically acceptable excipient.

* * * * *